(12) United States Patent
Cantore et al.

(10) Patent No.: US 12,359,217 B2
(45) Date of Patent: Jul. 15, 2025

(54) VIRUS VECTOR PRODUCTION

(71) Applicants: Ospedale San Raffaele S.r.l., Milan (IT); Fondazione Telethon ETS, Rome (IT)

(72) Inventors: Alessio Cantore, Milan (IT); Andrea Annoni, Milan (IT); Michela Milani, Milan (IT); Luigi Naldini, Milan (IT)

(73) Assignees: Ospedale San Raffaele S.r.l., Milan (IT); Fondazione Telethon ETS, Rome (IT)

( * ) Notice: Subject to any disclaimer, the term of this patent is extended or adjusted under 35 U.S.C. 154(b) by 1156 days.

(21) Appl. No.: 17/055,151

(22) PCT Filed: May 16, 2019

(86) PCT No.: PCT/EP2019/062664
§ 371 (c)(1),
(2) Date: Nov. 13, 2020

(87) PCT Pub. No.: WO2019/219836
PCT Pub. Date: Nov. 21, 2019

(65) Prior Publication Data
US 2021/0222197 A1    Jul. 22, 2021

(30) Foreign Application Priority Data
May 16, 2018 (GB) .................. 1807945

(51) Int. Cl.
C12N 15/86 (2006.01)
C12N 5/0783 (2010.01)
C12N 7/00 (2006.01)

(52) U.S. Cl.
CPC ........... *C12N 15/86* (2013.01); *C12N 5/0636* (2013.01); *C12N 7/00* (2013.01); *C12N 2510/02* (2013.01); *C12N 2740/10034* (2013.01); *C12N 2740/10052* (2013.01); *C12N 2740/15034* (2013.01); *C12N 2740/15052* (2013.01); *C12N 2740/16034* (2013.01); *C12N 2740/16043* (2013.01); *C12N 2740/16052* (2013.01)

(58) Field of Classification Search
CPC ........ C12N 15/86; C12N 5/0636; C12N 7/00; C12N 2510/02; C12N 2740/10034; C12N 2740/10052; C12N 2740/15034; C12N 2740/15052; C12N 2740/16034; C12N 2740/16043; C12N 2740/16052
See application file for complete search history.

(56) References Cited

U.S. PATENT DOCUMENTS

| 6,329,201 | B1 * | 12/2001 | Polo | C12N 15/86 |
| | | | | 435/352 |
| 10,912,824 | B2 * | 2/2021 | Cantore | A61P 7/02 |
| 2010/0316570 | A1 | 12/2010 | Discher et al. | |
| 2018/0214524 | A1 * | 8/2018 | Weissman | C07K 16/2803 |
| 2018/0355032 | A1 * | 12/2018 | Roberts | C12N 15/113 |
| 2019/0078096 | A1 | 3/2019 | Lahusen et al. | |
| 2021/0277354 | A1 | 9/2021 | Annoni et al. | |
| 2021/0346489 | A1 * | 11/2021 | Cantore | A61P 19/02 |

FOREIGN PATENT DOCUMENTS

| CN | 112601811 A | 4/2021 | | |
| IN | 201817003010 | 5/2018 | | |
| WO | WO-98/05635 A1 | 2/1998 | | |
| WO | WO-98/07859 A2 | 2/1998 | | |
| WO | WO-98/09985 A2 | 3/1998 | | |
| WO | WO-98/17815 A1 | 4/1998 | | |
| WO | WO-2009/131453 A1 | 10/2009 | | |
| WO | WO-2014/124028 A1 | 8/2014 | | |
| WO | WO-2015092440 A1 * | 6/2015 | ............ | A61K 48/00 |
| WO | WO-2016/009326 A1 | 1/2016 | | |
| WO | WO-2017/019848 A1 | 2/2017 | | |
| WO | WO-2017/088012 A1 | 6/2017 | | |
| WO | WO-2017/180519 A1 | 10/2017 | | |
| WO | WO-2017/184553 A1 | 10/2017 | | |
| WO | WO-2019086574 A1 * | 5/2019 | ............ | C07K 16/28 |

OTHER PUBLICATIONS

Matsunaga, Y. et al. (2008). Activation of Antigen-Specific Cytotoxic T Lymphocytes by β2-Microglobulin or TAP1 Gene Disruption and the Introduction of Recipient-Matched MHC Class I Gene in Allogeneic Embryonic Stem Cell-Derived Dendritic Cells. The Journal of Immunology (1950), 181(9), 6635-6643. (Year: 2008).*
Gornalusse, G. G. et al. (2017). HLA-E-expressing pluripotent stem cells escape allogeneic responses and lysis by NK cells. Nature Biotechnology, 35(8), 765-772. (Year: 2017).*
Cantore, A., Milani, M., Lengler, J., Bartolaccini, S., Di Tomaso, T., Gregory, P. D., Scheiflinger, F., Lombardo, A., & Naldini, L. (2015). 6. Targeted Genome Editing of Cell Lines for Improved and Scalable Production of Lentiviral Vectors for Human Gene Therapy. Molecular Therapy, 23, S3-S3. (Year: 2015).*
Cantore, A. et al. (2016). 286. Genome Editing of Inducible Cell Lines for Scalable Production of Improved Lentiviral Vectors for Human Gene Therapy. Molecular Therapy, 24, S115-S115. (Year: 2016).*
Cantore, A., Milani, M., Annoni, A., Liu, T., Bartolaccini, S., Biffi, M., Russo, F., Peters, R., Lombardo, A., Nichols, T. C., Ayuso, E., & Naldini, L. (2017). Liver-Directed Gene Therapy for Hemophilia B with Immune Stealth Lentiviral Vectors. Blood, 130, 605-605. (Year: 2017).*
Aiuti et al., Gene therapy for immunodeficiency due to adenosine deaminase deficiency, N. Engl. J. Med., 360(5):447-58 (Jan. 2009).
Aiuti et al., Lentiviral hematopoietic stem cell gene therapy in patients with Wiskott-Aldrich syndrome, Science, 341(6148):1233151 (Aug. 2013).

(Continued)

*Primary Examiner* — Janet L Andres
*Assistant Examiner* — Carey Alexander Stuart
(74) *Attorney, Agent, or Firm* — MARSHALL, GERSTEIN & BORUN LLP

(57) ABSTRACT

An enveloped viral particle producer or packaging cell, wherein the cell is genetically engineered to decrease expression of CD47 on the surface of the cell.

18 Claims, 8 Drawing Sheets

Specification includes a Sequence Listing.

(56) References Cited

OTHER PUBLICATIONS

Amabile et al., Inheritable Silencing of Endogenous Genes by Hit-and-Run Targeted Epigenetic Editing, Cell, 167(1):219-232.e14 (Sep. 2016).
Ausubel et al., Current Protocols in Molecular Biology, John Wiley and Sons, chapters 9, 13, 16 (1995).
Benechet et al., Intravital Microscopy Analysis of Hepatic T Cell Dynamics, Methods Mol. Biol., 14:49-61 (2017).
Biffi et al., Lentiviral hematopoietic stem cell gene therapy benefits metachromatic leukodystrophy, Science, 341(6148):1233158 (Aug. 2013).
Bobis-Wozowicz et al., Non-integrating gamma-retroviral vectors as a versatile tool for transient zinc-finger nuclease delivery, Scientific Reports, 4, article No. 4656 (2014).
Boztug et al., Stem-cell gene therapy for the Wiskott-Aldrich syndrome, N. Engl. J. Med., 363(20):1918-27 (Nov. 2010).
Cantore et al., Hyperfunctional coagulation factor IX improves the efficacy of gene therapy in hemophilic mice, Blood, 120(23):4517-20 (2012).
Cantore et al., Liver-directed lentiviral gene therapy in a dog model of hemophilia B, Science Translational Medicine, 7, pp. 277ra28 (2015).
Cartier et al., Hematopoietic stem cell gene therapy with a lentiviral vector in X-linked adrenoleukodystrophy, Science, 326(5954):818-23 (Nov. 2009).
Coffin et al., Retroviral taxonomy, protein structures, sequences and genetic maps, IN: Retroviruses, Cold Spring Harbour Laboratory Press, pp. 758-763 (1997).
Ewer et al. , A Monovalent Chimpanzee Adenovirus Ebola Vaccine Boosted with MVA, New England J Medicine, 2015, vol. 374, pp. 1635-1646.
Gait, Oligonucleotide Synthesis: A Practical Approach, IRL Press (1984). [Table of Contes].
Gaj et al, ZFN, TALEN and CRISPR/Cas-based methods for genome engineering, Trends Biotechnol., vol. 31, pp. 397-405 (2013).
GenBank Accession No. NM_004048, May 3, 2014.
Hacien-Bey-Abina et al., Efficacy of gene therapy for X-linked severe combined immunodeficiency, N. Engl. J. Med., 363(4):355-64 (Jul. 2010).
International Application No. PCT/EP2019/062664, International Search Report and Written Opinion, mailed Aug. 19, 2019.
Koh et al., Exosome-SIRPa, a CD47 blockade increases cancer cell phagocytosis, Biomaterials, 2017, No. 121, pp. 121-129.
Leavitt et al., Human immunodeficiency virus type 1 integrase mutants retain in vitro integrase activity yet fail to integrate viral DNA efficiently during infection, J Virol, vol. 70, pp. 721-728 (1996).
Lee et al., CD47 Plays a role as a negative regulator in inducing protective immune responses to vaccination against influenza virus, Journal of Virology, Aug. 2016, vol. 90, No. 15, pp. 6746-6758.
Lewis et al., Human immunodeficiency virus infection of cells arrested in the cell cycle, EMBO J, vol. 11, pp. 3053-3058 (1992).
Lewis et al., Passage through mitosis is required for oncoretroviruses but not for the human immunodeficiency virus, J Virol, vol. 68, pp. 510-516 (1994).
Lichty et al., Going viral with cancer immunotherapy, Nat. Rev. Cancer, 14(8):559-67 (2014).
Lilley et al. (eds.), DNA Structures, Part A, Synthesis and Physical Analysis of DNA, vol. 211 in Methods in Enzymology, San Diego, California: Academic Press, Inc. (1992).
Lombardo et al., Site-specific integration and tailoring of cassette design for sustainable gene transfer, Nat Methods, 2011, vol. 8, pp. 861-869.

Maetzig et al., Retroviral protein transfer: falling apart to make an impact, Current Gene Ther, vol. 12, pp. 389-409 (2012).
Matsui et al., A microRNA-regulated and GP64-pseudotyped lentiviral vector mediates stable expression of FVIII in a murine model of Hemophilia A, Mol. Ther., 19(4):723-30 (Apr. 2011).
Milani et al., Genome editing for scalable production of alloantigen-free lentiviral vectors for in vivo gene therapy, EMBO Mol. Med., 9(11):1558-73 (Nov. 2017).
Milani et al., Phagocytosis-shielded lentiviral vectors improve liver gene therapy in nonhuman primates, Sci. Transl. Med, May 22, 2019, vol. 11(493): eaav7325.
Naldini et al., Efficient transfer, integration, and sustained long-term expression of the transgene in adult rat brains injected with a lentiviral vector, Proc. Natl. Acad. Sci. USA, vol. 93, pp. 11382-11388 (1996).
Naldini et al., In vivo gene delivery and stable transduction of nondividing cells by a lentiviral vector, Science, vol. 272, pp. 263-267 (1996).
Nightingale et al., Transient gene expression by nonintegrating lentiviral vectors, Mol. Ther, vol. 13, pp. 1121-1132 (2006).
Oldenborg et al., Role of CD47 as a Marker of Self on Red Blood Cells, Science, Jun. 16, 2000, vol. 288(5473), pp. 2051-2054.
Penn, Major Histocompatibility Complex (MHC), Encyclopedia of Life Sciences, John Wiley & Sons (2005).
Polak et al. (eds.), In Situ Hybridization: Principles and Practice, New York: Oxford University Press (1990) [Table of Contents].
Rodriguez et al., Minimal "Self" Peptides That Inhibit Phagocytic Clearance and Enhance Delivery of Nanoparticles, Science, Feb. 22, 2013, vol. 339, pp. 971-974.
Roe et al., DNA Isolation and Sequencing: Essential Techniques, Chichester, West Sussex: John Wiley & Sons (1996). [Table of Contents].
Sambrook et al., Molecular Cloning: a Laboratory Manual, Cold Harbor Laboratory, 2nd edition (1989), [Table of Contents].
Sosale et al., "Marker of Self" CD47 on lentiviral vectors decreases macrophage-mediated clearance and increases delivery to SIRPA-expressing lung carcinoma tumors, Molecular Therapy—Methods & Clinical Development, 3:16080 (2016).
Sosale et al., Reducing Immune Response against Lentiviral Vectors; Lentiviral Vector Presentation of CD47, the "Marker of Self", Biophysical Journal, 2011, vol. 100, issue 3, supplement 1, p. 403a, abstract 2181-Pos Board B167.
Sosale, Inhibiting Phagocytosis with Cd47: from the effects of red cell rigidity and shape to display on lentivirus—implications for aging and gene therapy, University of Pennsylvania Dissertations, Jan. 1, 2014, No. 1451.
Tseng et al., Anti-CD47 antibody-mediated phagocytosis of cancer by macrophages primes an effective antitumor T-cell response, Proc Natl Acad Sci., Jul. 2, 2013, vol. 110, No. 27, pp. 11103-11108.
Voelkel et al., Protein transduction from retroviral Gag precursors, Proc National Acad Sci USA, vol. 107, No. 17, pp. 7805-7810 (2010).
Wu et al., Critical role of integrin CD11c in splenic dendritic cell capture of missing-self CD47 cells to induce adaptive immunity, Proc. Natl. Acad. Sci. USA, 115(26):6786-91 (Jun. 2018).
Cantore et al., Efficacy and safety of liver-directed lentiviral gene therapy in hemophilia B dogs and non-human primates, Mol. Ther., 25(5 Suppl 1):30-31 Abstract (2017).
Milone et al., Clinical use of lentiviral vectors, Leukemia, 32(7):1529-41 (2018).
Toledano et al., Novel CD47: SIRPα dependent mechanism for the activation of STAT3 in antigen-presenting cell, PLoS One, 8(9):e75595 (2013).
Bai et al., Achievements and concerns of the CD47 targeted anti-cancer therapy, Chin J Clin Oncol., 44(7): 344-348 (2017).
Gao et al., Effect of small interfering RNA targeting CD47 gene mediated by lentivirus vectors on proliferation and apoptosis of human laryngocarcinoma Hep-2 cells, Med J Chin PLA, 38(8): 634-638 (2013).

\* cited by examiner

VIRUS VECTOR PRODUCTION

CROSS-REFERENCE TO RELATED APPLICATIONS

This application is a U.S. National Phase of International Patent Application No. PCT/EP2019/062664, filed on May 16, 2019, which claims priority to United Kingdom Patent Application No. 1807945.9, filed on May 16, 2018.

INCORPORATION BY REFERENCE OF MATERIAL SUBMITTED ELECTRONICALLY

A Sequence Listing, submitted as part of the specification as a text file, is incorporated herein by reference. The file containing the Sequence Listing is "56092_Seqlisting", created on Nov. 11, 2020, and is 15,339 bytes in size.

FIELD OF THE INVENTION

The present invention relates to cells that display decreased levels of surface-exposed antigens. More specifically, the invention relates to the genetic engineering of cells to decrease the expression of CD47 on the surface of the cells. In particular, the invention relates to the use of such cells in the production of enveloped viral particles.

BACKGROUND TO THE INVENTION

Gene therapy involves the incorporation of genetic material into a cell to treat or prevent disease. The genetic material may supplement defective genes with functional copies of those genes, inactivate improperly functioning genes or introduce genes to instruct new functions to a cell.

Delivery of genetic material to a cell may be achieved through use of vectors which facilitate the transfer of nucleic acids. Viruses may be engineered to deliver a nucleotide of interest (NOI) to a target cell and are commonly employed as vectors in gene therapy. Viruses that have been used in gene therapy to date include retroviruses, adenoviruses (AdV), adeno-associated viruses (AAV), herpes simplex viruses (HSV) and vaccinia viruses.

Retroviruses, for example α-retroviruses, γ-retroviruses, lentiviruses and spumaviruses, are particularly useful for gene therapy as they permit stable integration of the corrective genetic material into the target cell. Therapeutic benefits have already been achieved in clinical trials based on γ-retrovirus-derived vectors for Adenosine Deaminase Severe Combined Immunodeficiency (ADA-SCID; Aiuti, A. et al. (2009) N. Engl. J. Med. 360:447-58), X-linked Severe Combined Immunodeficiency (SCID-X1; Hacein-Bey-Abina, S. et al. (2010) N. Engl. J. Med. 363:355-64) and Wiskott-Aldrich syndrome (WAS; Boztug, K. et al. (2010) N. Engl. J. Med. 363:1918-27). In addition, lentiviral vectors have been employed as delivery vehicles in the treatment of X-linked adrenoleukodystrophy (ALD; Cartier, N. et al. (2009) Science 326:818-23), and of metachromatic leukodystrophy (MLD; Biffi, A. et al. (2013) Science 341: 1233158) and WAS (Aiuti, A. et al. (2013) Science 341: 1233151). In pre-clinical studies, lentiviral vectors have also been administered intravenously for liver-directed gene therapy of haemophilia in mice and dog models of the disease (Cantore, A. et al. (2012) Blood; Matsui, H. et al. (2011) Mol Ther; Cantore, A. et al. (2015) Science Translational Medicine 7: 277ra28).

Efforts have been made to obtain gene therapy vectors able to escape immune cell sensing for their application in stable gene replacement therapy strategies for genetic diseases. However, there are a number of applications of gene transfer vectors that require efficient gene delivery to innate immune cells, for example the use of vectors as oncolytic viruses (Lichty, B. D. et al. (2014) Nature Rev Cancer 14:559-567) and for vaccination purposes (Rampling et al. (2015) NEJM).

A viral particle envelope typically originates in a membrane of the producer cell. Therefore, membrane proteins that are expressed on the cell membrane from which the viral particle buds may be incorporated into the viral envelope. Such surface-exposed proteins may impact on the utility of the viral particles as gene therapy vectors, for example by improving or preventing transduction of certain types of cell, or giving rise to deleterious immune responses against the viral particles or the cells they transduce. Conversely, stimulation of the immune system may be desirable for certain utilities, for example vaccination purposes.

Accordingly, there exists a significant need in the art for viral vector particles that have improved characteristics of cell transduction, and stimulation or evasion of immune responses.

SUMMARY OF THE INVENTION

The inventors have surprisingly found that gene transfer into professional phagocytes and antigen presenting cells (APCs) is constrained by the presence of the CD47 molecules on LV particles.

By genetically disrupting the CD47 gene in cells used for the production of LV particles, the inventors were able to modify the protein composition of the LV envelope and obtained LV particles lacking human CD47 on their surface (CD47-free LV). Surprisingly, the inventors have shown that the absence of surface-exposed CD47 molecules is not toxic for the cells and does not significantly affect the ability of these cells to produce enveloped viral particles.

Furthermore, the inventors have demonstrated that the CD47-free LV show preserved infectivity and substantially increased susceptibility to phagocytosis. The CD47-free LV more efficiently transduce professional phagocytes both ex vivo and in vivo, and induce a substantially higher rise in cytokine response upon systemic administration to mice, compared to CD47-bearing LV. The CD47-free LV allow increased gene transfer efficiency into human primary monocytes, and have increased susceptibility to phagocytosis both ex vivo by primary human macrophages and in vivo when administered systemically to mice, compared to previously available LV.

There are numerous pathways involved in phagocytosis and viral vector uptake and entry, prior to the inventors' discovery it is was not apparent that LV lacking surface-exposed CD47 would show increased efficiency of gene transfer into APCs. Furthermore, it was not apparent that the interaction between VSV-G and its receptor on target cells can be negatively affected by the presence of the CD47 signal on the viral particle.

The engineered CD47-negative cells can be used to produce LV and other enveloped viral vector particles, which are suitable, for example, for gene transfer into professional phagocytes for application in vaccination, immune modulation and cancer immunotherapy. CD47-free LV can be used to transfer genes into professional APCs, broadening the applicability of LV outside genetic diseases to indications such as cancer-targeted immunotherapy strategies, infectious diseases and for vaccination purposes. Indeed, the inventors have shown that when administered in vivo, CD47-free LV induce greater release of cytokines and chemokines, which is crucial when the goal of the therapy is to induce an immune response. CD47-free LV can be used also for targeting macrophages when they are involved in infectious or immune mediated diseases, such as in HIV infection, or inflammatory bowel disease or other autoimmune or autoinflammatory diseases.

In one aspect the invention provides an enveloped viral particle producer cell, wherein the cell is genetically engineered to decrease expression of CD47 on the surface of the cell.

In one aspect the invention provides an enveloped viral particle packaging cell, wherein the cell is genetically engineered to decrease expression of CD47 on the surface of the cell.

In one embodiment, the cell comprises a genetically engineered disruption of a gene encoding CD47. The cell may comprise genetically engineered disruptions in all copies of the gene encoding CD47.

The expression of CD47 on the surface of the cell may be decreased such that the cell is substantially devoid of surface-exposed CD47 molecules. In one embodiment, the cell does not comprise any surface-exposed CD47 molecules.

In one embodiment, the cell is further genetically engineered to decrease expression of MHC-I on the surface of the cell. In one embodiment, the cell comprises a genetically engineered disruption of a gene encoding β2-microglobulin. In one embodiment, the cell comprises a genetically engineered disruption of one or more genes encoding an MHC-I α chain. The cell may comprise genetically engineered disruptions in all copies of the gene encoding 32-microglobulin. The cell may comprise genetically engineered disruptions in all copies of the genes encoding an MHC-I α chain. The cell may comprise both genetically engineered disruptions of genes encoding β2-microglobulin and genetically engineered disruptions of genes encoding an MHC-I α chain.

The expression of MHC-I on the surface of the cell may be decreased such that the cell is substantially devoid of surface-exposed MHC-I molecules. In one embodiment, the cell does not comprise any surface-exposed MHC-I molecules.

The term viral particle "producer cell" includes a cell that produces viral particles, after transient transfection, stable transfection or vector transduction of all the elements necessary to produce the viral particles or any cell engineered to stably comprise the elements necessary to produce the viral particles.

The term "packaging cell" includes a cell which contains some or all of the elements necessary for packaging an infectious recombinant virus. The packaging cell may lack a recombinant viral vector genome. Typically, such packaging cells contain one or more vectors which are capable of expressing viral structural proteins. Cells comprising only some of the elements required for the production of enveloped viral particles are useful as intermediate reagents in the generation of viral particle producer cell lines, through subsequent steps of transient transfection, transduction or stable integration of each additional required element. These intermediate reagents are encompassed by the term "packaging cell". Parental cells to be subsequently used for the generation of enveloped viral particle producer or packaging cell lines, in which the expression of CD47 on the surface of the cell has been decreased are also encompassed by the present invention.

Viral particles referred to herein encompass replication-competent or -defective viruses, viral vectors derived therefrom, and may or may not comprise a nucleotide of interest.

In one embodiment, the enveloped viral particle producer or packaging cell is a HEK-293 cell or a derivative thereof. In one embodiment, the enveloped viral particle producer or packaging cell is a HEK-293T or a HEK-293 T-REx cell.

In one embodiment, the enveloped viral particle is a retroviral, herpes simplex viral, vaccinia viral, hepadnaviral, togaviral, flaviviral, arenaviral, coronaviral, orthomyxoviral, paramyxoviral, bunyaviral, bornaviral, rhabdoviral or filoviral particle, or a viral particle derived therefrom.

In one embodiment, the enveloped viral particle is a retroviral, herpes simplex viral or vaccinia viral particle, or a viral particle derived therefrom In a preferred embodiment, the enveloped viral particle is a lentiviral particle or a viral particle derived therefrom. In one embodiment, the enveloped viral particle is a HIV-1 particle or a viral particle derived therefrom.

In another aspect, the invention provides a population of enveloped viral particle producer or packaging cells of the invention.

In one embodiment, at least about 50%, 60%, 70%, 75%, 80%, 85%, 90%, 95%, 96%, 97%, 98%, 99% or 100% of the cells in the population have been genetically engineered according to the present invention.

In another aspect, the invention provides a parental cell for the generation of enveloped viral particle producer or packaging cell lines according to the invention, wherein the parental cell is genetically engineered to decrease expression of CD47 on the surface of the cell.

In another aspect, the invention provides use of the enveloped viral particle producer cell of any preceding claim for the production of enveloped viral particles.

In one embodiment, the enveloped viral vector particles comprise less than about 50%, 40%, 30%, 25%, 20%, 15%, 10%, 5%, 4%, 3%, 2% or 1% of the number of surface-exposed CD47 molecules that are displayed on particles produced by enveloped viral particle producer cells in the absence of the genetic engineering (but under otherwise substantially identical conditions).

In one embodiment, the enveloped viral particles do not comprise any surface-exposed CD47 molecules. In one embodiment, the enveloped viral particles are substantially devoid of surface-exposed CD47 molecules.

In another aspect, the invention provides a method of producing enveloped viral particles comprising the steps of:
a) providing an enveloped viral particle producer cell according to the invention; and
b) culturing the cell under conditions suitable for the production of the enveloped viral particles.

In another aspect, the invention provides an enveloped viral particle obtainable by the enveloped viral particle production method of the invention.

In one embodiment, the enveloped viral vector particles comprise less than about 50%, 40%, 30%, 25%, 20%, 15%, 10%, 5%, 4%, 3%, 2% or 1% of the number of surface-exposed CD47 molecules that are displayed on particles produced by enveloped viral particle producer cells in the absence of the genetic engineering (but under otherwise substantially identical conditions).

In one embodiment, the enveloped viral particle does not comprise any surface-exposed CD47 molecules. In one embodiment, the enveloped viral particle is substantially devoid of surface-exposed CD47 molecules.

In one embodiment, the enveloped viral particle is a retroviral, herpes simplex viral, vaccinia viral, hepadnaviral, togaviral, flaviviral, arenaviral, coronaviral, orthomyxoviral, paramyxoviral, bunyaviral, bornaviral, rhabdoviral or filoviral particle, or a viral particle derived therefrom.

In one embodiment, the enveloped viral particle is a retroviral, herpes simplex viral or vaccinia viral particle, or a viral particle derived therefrom In a preferred embodiment, the enveloped viral particle is a lentiviral particle or a viral particle derived therefrom. In one embodiment, the enveloped viral particle is a HIV-1 particle or a viral particle derived therefrom.

In one embodiment, the enveloped viral particles of the invention are used for protein transfer (Bobis-Wozowicz, S. et al. (2014) Sci Rep; Voelkel, C. et al. (2010) Proc Natl Acad Sci USA; Maetzig, T. et al. (2012) Curr Gene Ther).

In one embodiment, the enveloped viral particle comprises a nucleotide of interest (NOI). Preferably, the enveloped viral particle is an attenuated virus, for example a replication deficient virus.

In one embodiment, the enveloped viral particle comprises a transgene encoding a cytokine.

In another aspect, the invention provides a population of enveloped viral particles of the invention.

In one embodiment, at least about 50%, 60%, 70%, 75%, 80%, 85%, 90%, 95%, 96%, 97%, 98% or 99% of the particles in the population originate from an enveloped viral particle producer cell of the invention. In one embodiment, 100% of the particles in the population originate from an enveloped viral particle producer cell of the invention. In one embodiment, the particles in the population substantially do not comprise surface-exposed CD47.

In another aspect, the invention provides use of an enveloped viral particle of the invention for transducing a macrophage, phagocyte, antigen-presenting cell or monocyte.

In another aspect, the invention provides use of an enveloped viral particle of the invention for transducing a liver macrophage.

In one embodiment, the enveloped viral particle is used for transducing a macrophage, for example a Kupffer cell. In one embodiment, the enveloped viral particle is used for transducing a phagocyte. In one embodiment, the enveloped viral particle is used for transducing an antigen-presenting cell, for example a dendritic cell, plasmacytoid dendritic cell (pDC) or a myeloid dendritic cell (myDC). In one embodiment, the enveloped viral particle is used for transducing a monocyte.

In one embodiment, the transduction is in vitro, ex vivo or in vivo transduction. In one embodiment, the transduction is in vitro transduction. In one embodiment, the transduction is ex vivo transduction.

In one embodiment, the enveloped viral particle is administered to a subject systemically.

In another aspect, the invention provides a cell transduced by the enveloped viral particle of the invention. The cell may be a mammalian cell, for example a primate cell or a human cell.

In one embodiment, the cell is a macrophage (e.g. a Kupffer cell), phagocyte, antigen-presenting cell (e.g. a dendritic cell, a plasmacytoid dendritic cell, pDC or a myeloid dendritic cell, myDC) or monocyte. In one embodiment, the cell is a liver macrophage.

In another aspect, the invention provides a pharmaceutical composition comprising the enveloped viral particle or the transduced cell of the invention, and a pharmaceutically-acceptable carrier, diluent or excipient.

In another aspect, the invention provides the enveloped viral particle of the invention for use in therapy. The enveloped viral particle of the invention may be used in gene therapy.

In another aspect, the invention provides the transduced cell of the invention for use in therapy. The transduced cell of the invention may be used in gene therapy.

In another aspect, the invention provides the enveloped viral particle of the invention for use in the treatment or prevention of cancer. In another aspect, the invention provides the enveloped viral particle of the invention for use in the treatment or prevention of bacterial or viral infection. In another aspect, the invention provides the enveloped viral particle of the invention for use in the treatment or prevention of an immune-mediated disease or autoimmune disease.

In another aspect, the invention provides the transduced cell of the invention for use in the treatment or prevention of cancer. In another aspect, the invention provides the transduced cell of the invention for use in the treatment or prevention of bacterial or viral infection. In another aspect, the invention provides the transduced cell of the invention for use in the treatment or prevention of an immune-mediated disease or autoimmune disease.

In another aspect, the invention provides the enveloped viral particle of the invention for use in vaccination or gene therapy, preferably for use in the treatment or prevention of cancer, bacterial or viral infection, an immune-mediated disease or autoimmune disease.

In another aspect, the invention provides the transduced cell of the invention for use in vaccination or gene therapy, preferably for use in the treatment or prevention of cancer, bacterial or viral infection, an immune-mediated disease or autoimmune disease.

In another aspect, the invention provides a method of treatment of cancer, bacterial or viral infection, an immune-mediated disease or autoimmune disease comprising transducing a cell with the enveloped viral particle of the invention.

In one embodiment, the transduction is in vitro, ex vivo or in vivo transduction. In one embodiment, the transduction is in vitro transduction. In one embodiment, the transduction is ex vivo transduction.

In another aspect, the invention provides a method of treatment of cancer, bacterial or viral infection, an immune-mediated disease or autoimmune disease comprising administering the enveloped viral particle or the cell of the invention to a subject in need thereof.

In one embodiment, the enveloped viral particle is administered to a subject systemically.

In another aspect, the invention provides the enveloped viral particle of the invention for use as a vaccine.

In another aspect, the invention provides a method of vaccination comprising administering the enveloped viral particle of the invention to a subject in need thereof.

infectious titre (TU/mL); (d) physical particles (ng p24/mL); and (e) specific infectivity (TU/ng p24) of LV produced by CD47-positive (black bars, n=3) or by CD47-negative (white bars, n=3) 293T as indicated. No significant differences by Mann-Whitney test.

Figure 2:
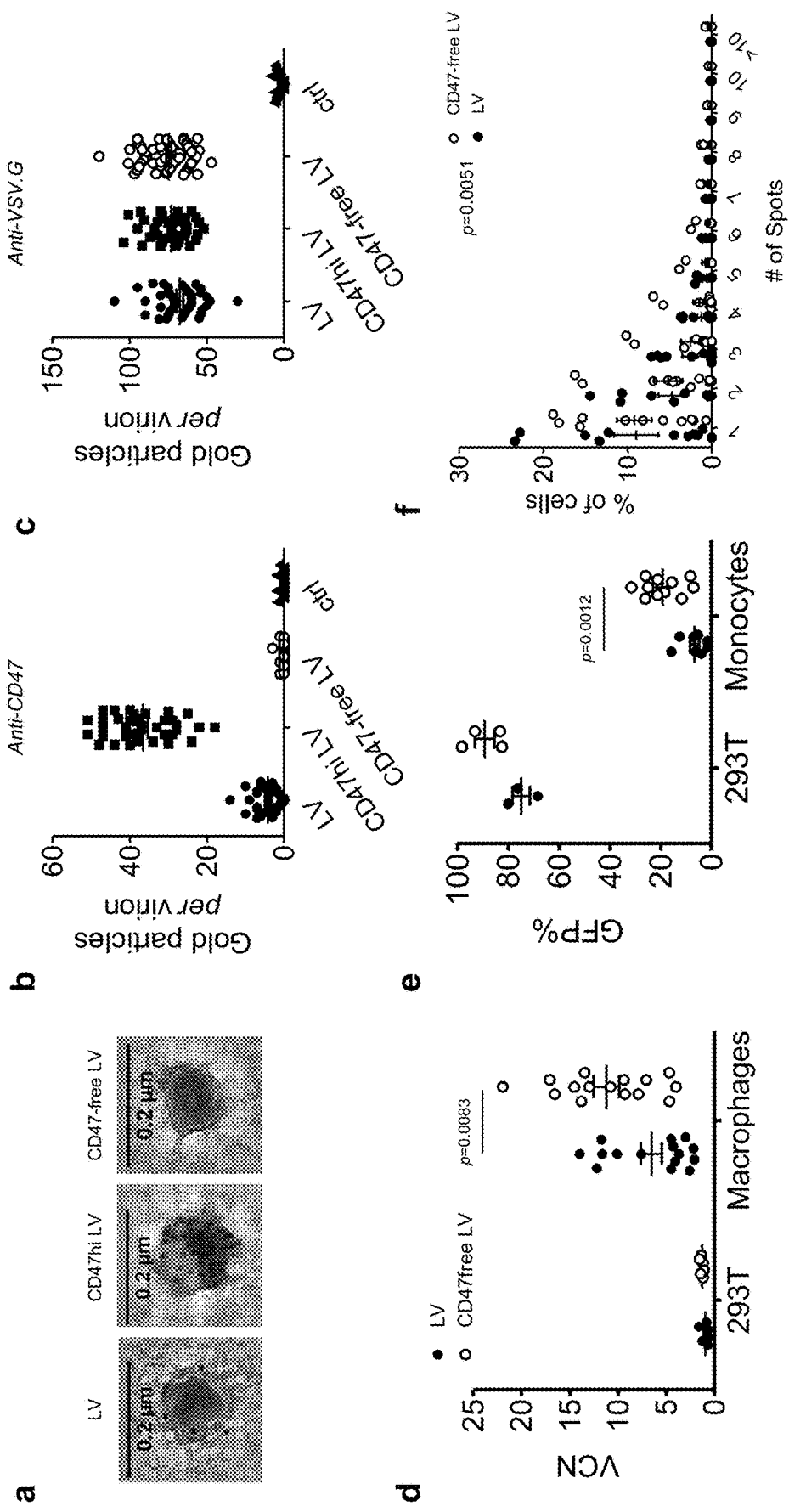

FIG. 2 Generation, imaging and in vitro evaluation of CD47-free LV. (a-c) Representative photomicrographs (a) and quantitative analysis (c, d) of LV batches produced by control (LV, black circles), CD47-overexpressing (CD47hi LV, black squares), or CD47-negative 293T cells (CD47-free LV, white circles), immunostained with anti-CD47 (b) or anti-VSV.G (c) antibodies (as indicated) or as staining control without the primary antibody (ctrl, black triangles) and analysed by electron microscopy (n=41-70 virions per sample). Kruskal-Wallis test with Dunn's multiple comparison test. (d) Single values and mean with SEM of VCN in 293T cells and primary human macrophages (n=6 for 293T, n=15 for macrophages) transduced with LV (black circles) or CD47-free LV (white circles) at MOI 10 and analysed 3 days after transduction (2 independent experiments with 5 different healthy blood donors). (e) Single values and mean with SEM of percentage of GFP-positive cells in 293T cells and primary human dendritic cells (n=3-4 for 293T, n=8-11 for dendritic cells) transduced with LV (black circles) or CD47-free LV (white circles) at MOI 3 and analysed 3 days after transduction. Please note that dendritic cells are transduced at day 2 of the differentiation protocol starting from human primary monocytes. Mann-Whitney test. (f) Mean and SEM with single values of percentage of primary human macrophages displaying the number of LV spots indicated on the X axis analysed by ImageStream after incubation with LV (black spots) or CD47-free LV (white dots) (8 independent experiments performed with macrophages derived from 11 different normal donors). Wilcoxon matched pairs test. VSV.G: Vesicular Stomatitis Virus G protein.

Figure 3:
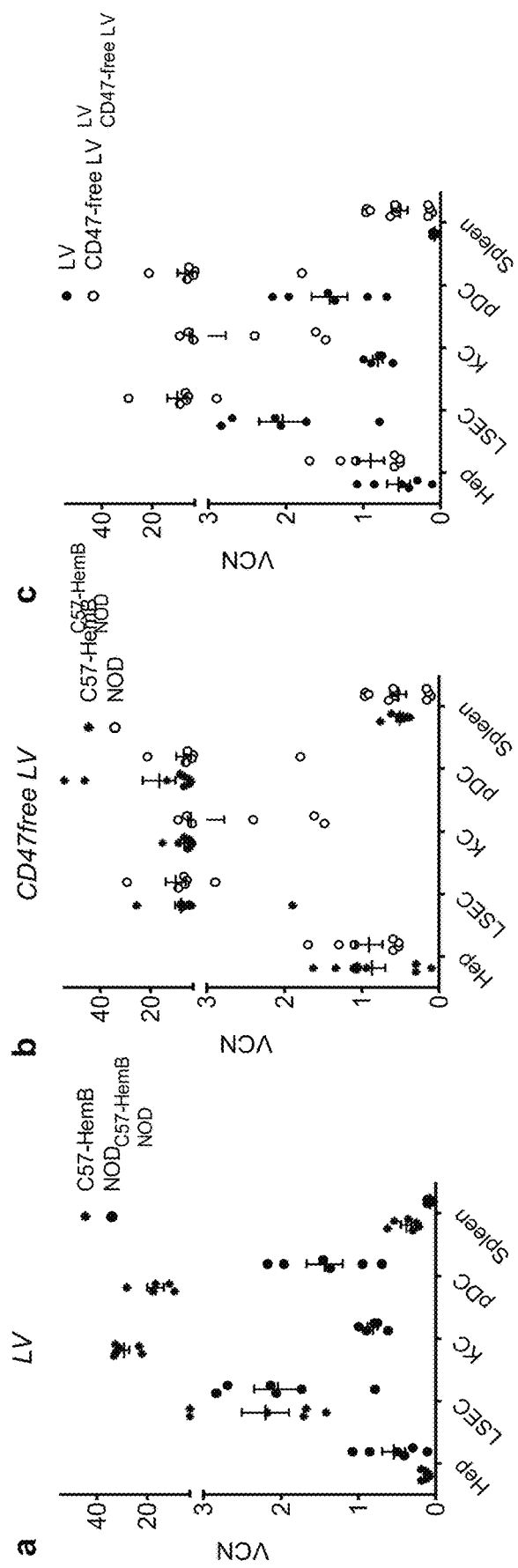

FIG. 3 In vivo evaluation of CD47-free LV. (a-c) Single values and mean with SEM of VCN in FACS-sorted hepatocytes (Hep), liver sinusoidal endothelial cells (LSEC), Kupffer cells (KC) or plasmacytoid dendritic cells (pDC), and whole spleen (as indicated) of C57 BL/6 haemophilia B (n=5-9, black stars) or NOD (n=5-11, black circles) mice injected with LV (a) or CD47free LV (b) (n=11-16, n=4 for pDC) at $1.2-2\times10^{10}$ TU/kg. VCN measured 2 months after LV administration. Mann-Whitney test. In (c) we report the same data sets shown in (a) (LV-treated NOD mice) and in (b) (CD47-free LV treated NOD mice) but plotted here together for direct comparison of LV and CD47-free LV in the same mouse strain (NOD).

Figure 4:
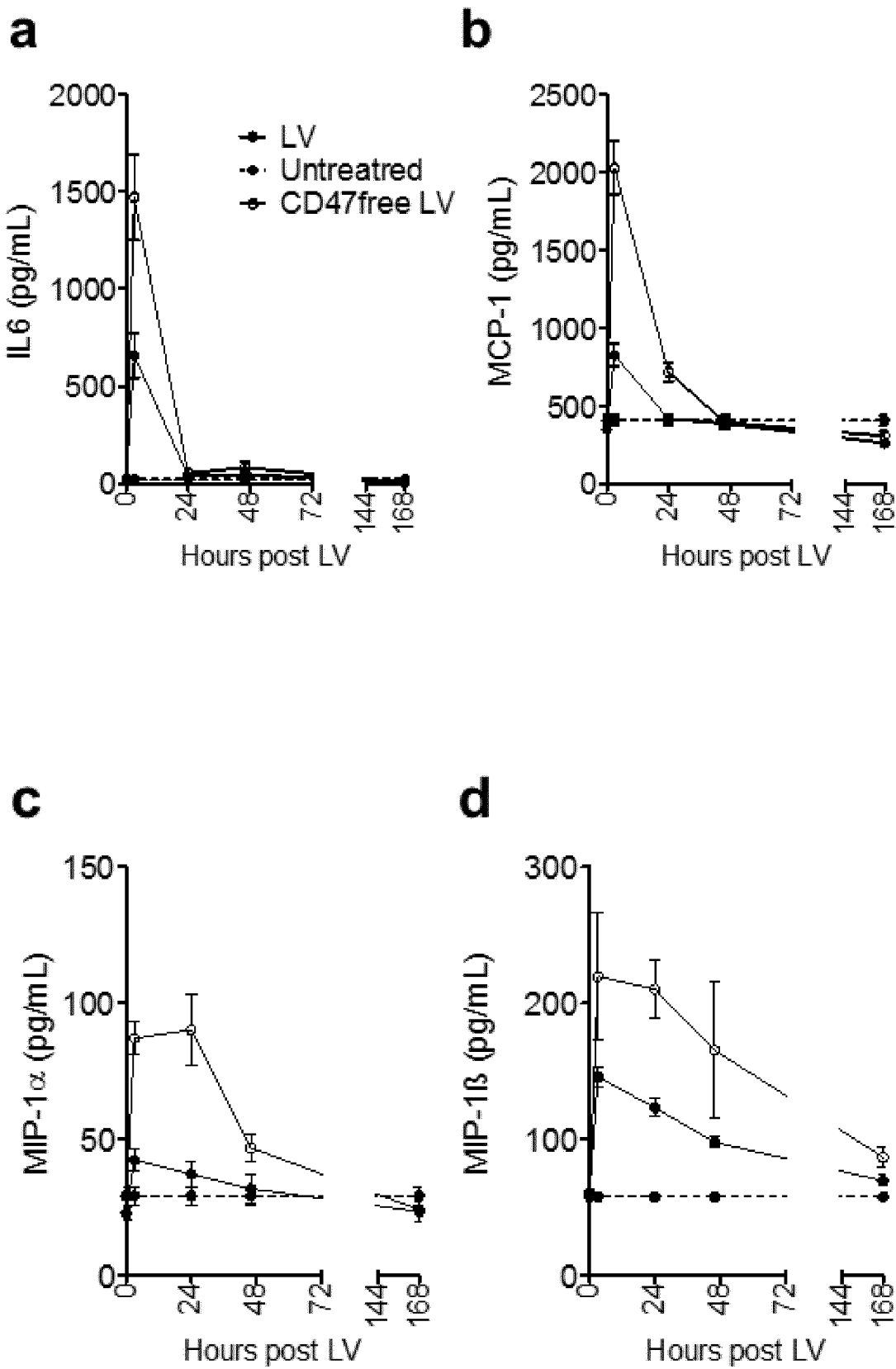
Figure 4:
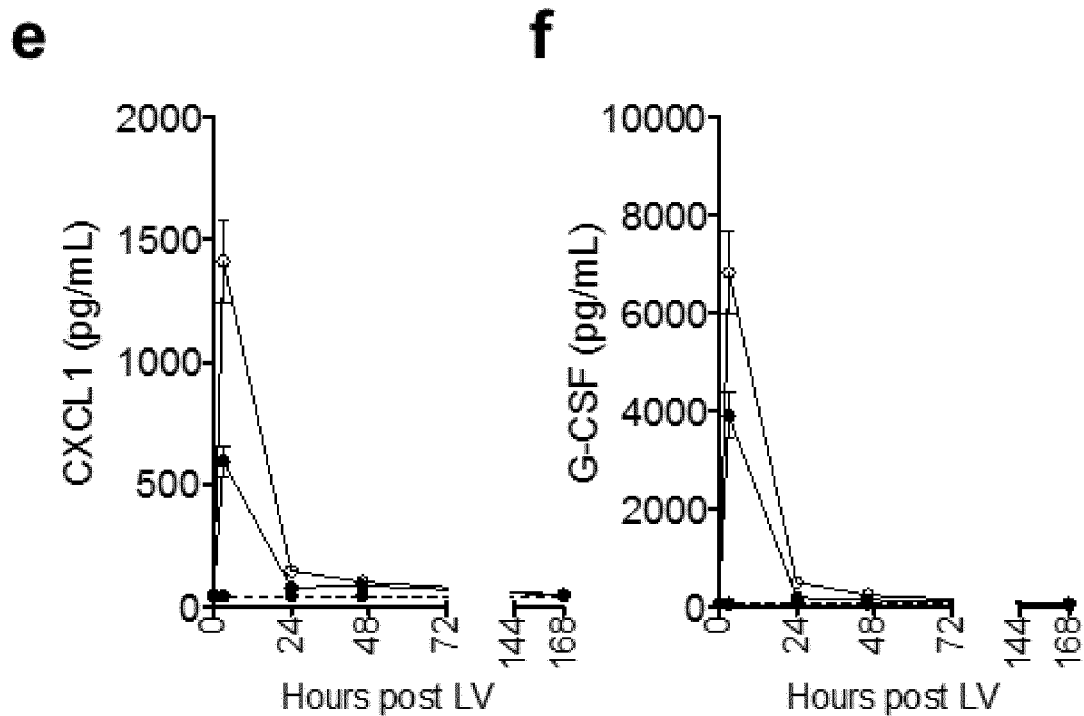
Figure 4:
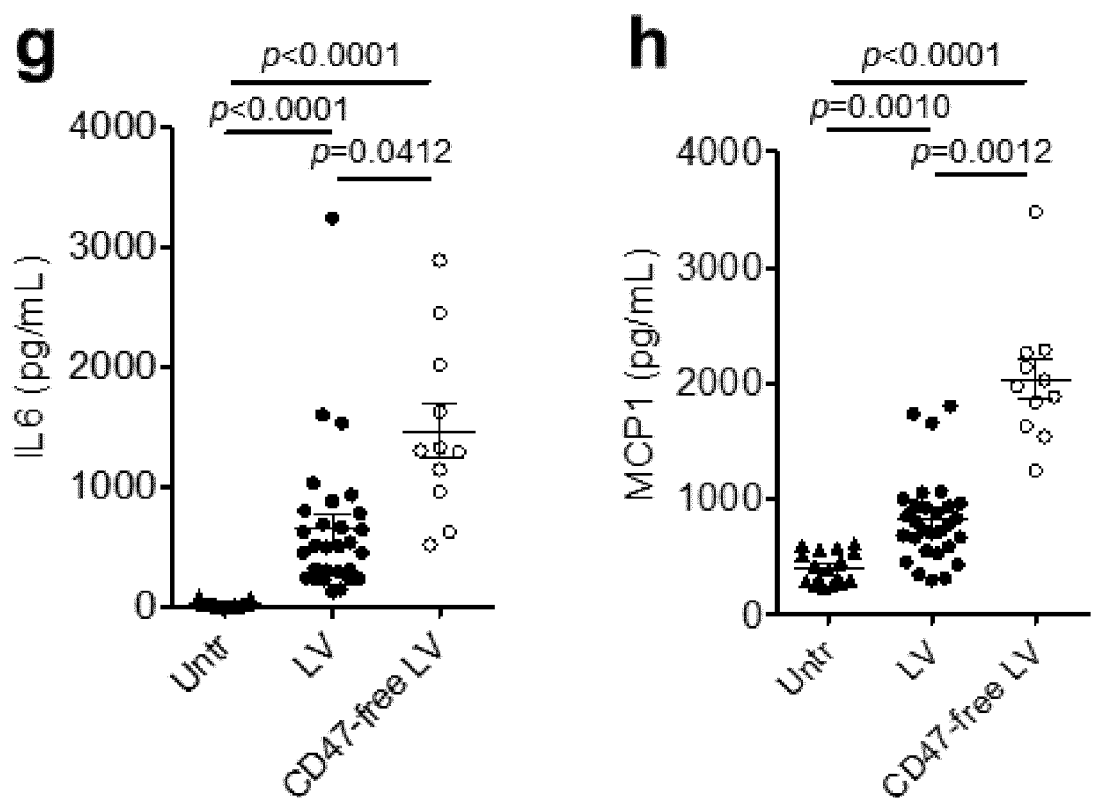
Figure 4:
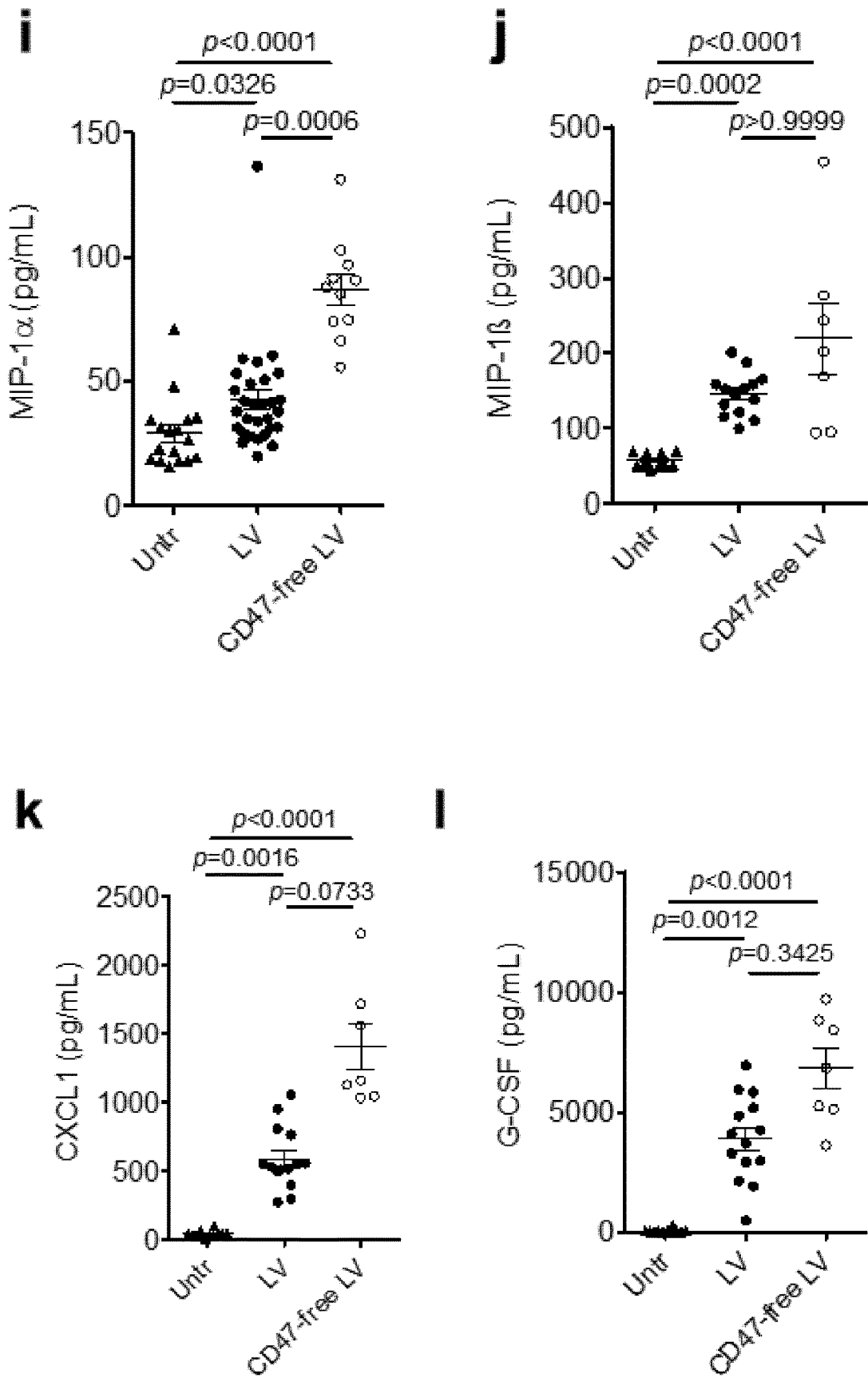

FIG. 4 CD47-free LV administration results in higher pro-inflammatory cytokine response. (a-l) Mean with SEM of the concentration of IL-6 (a, g), MCP-1 (b, h), MIP-1a (c, i), MIP-1β (d, j), CXCL1 (e, k) and G-CSF (f, l) in the serum of NOD mice, (a-f) at the indicated time (hours) after administration of LV (black circles) or CD47-free LV (white circles) or at peak (g-l, 3 hours post LV administration). The dashed lines show the mean concentration in untreated cohorts. Kruskal-Wallis test with Dunn's multiple comparison test.

Figure 5:
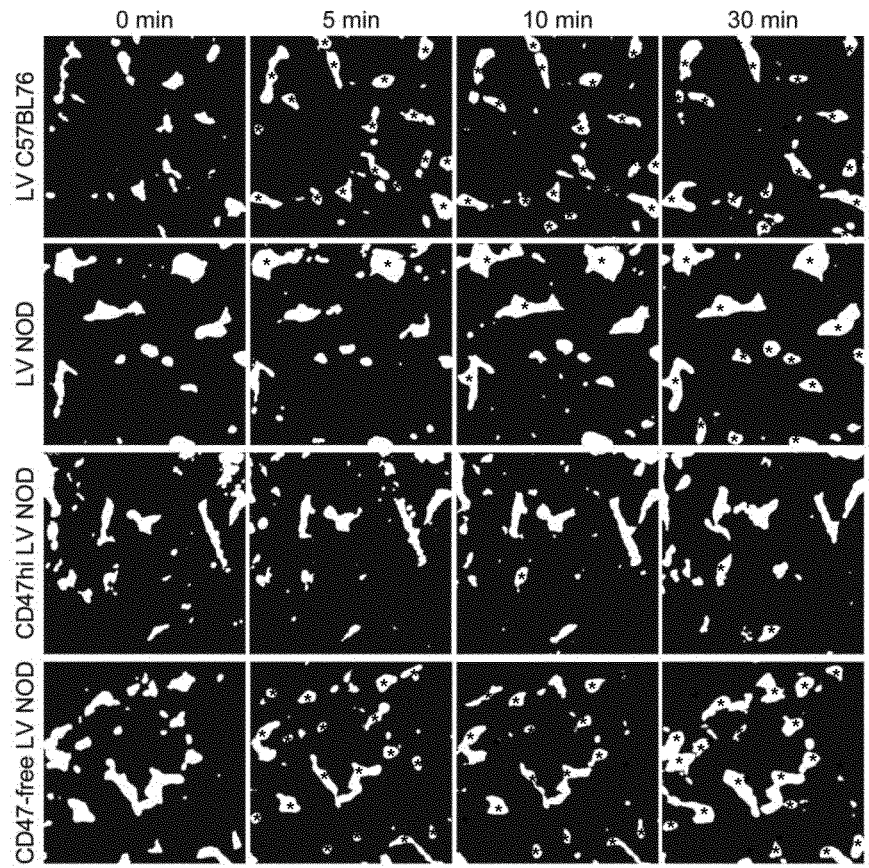
Figure 5:
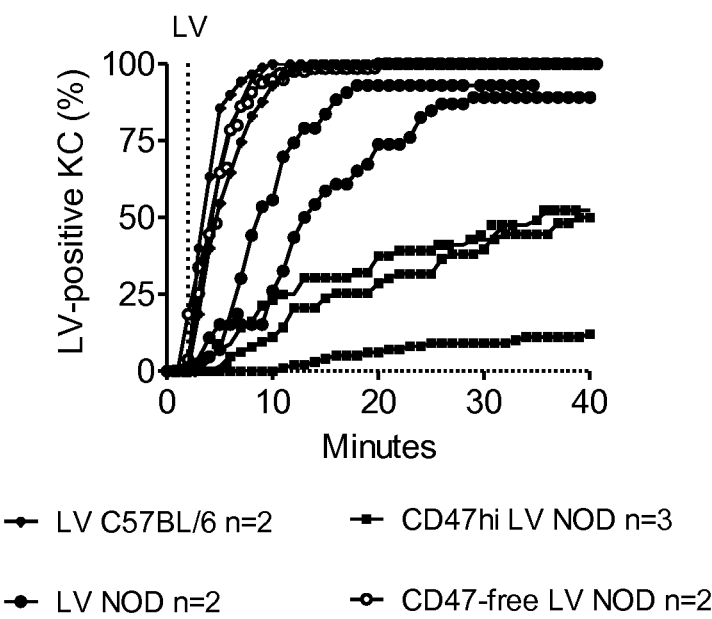

FIG. 5 Intravital imaging of LV, CD47hi or CD47-free LV uptake by liver Kupffer cells (KC) in mice. (a) Intravital 2-photon microscope images from 8-12 z-stacks spacing 4 μm of livers of C57BL/6 or NOD mice treated with GFP-labelled LV, CD47hi or CD47-free LV as indicated, at the indicated time (minutes; LV intravenous injection starts at min 2). KC are shown in white. LV-positive KC are marked with an asterisk. (b) Percentage of LV-positive KC over time in C57BL/6 or NOD mice treated with LV, CD47hi or CD47-free LV as indicated.

Figure 6:
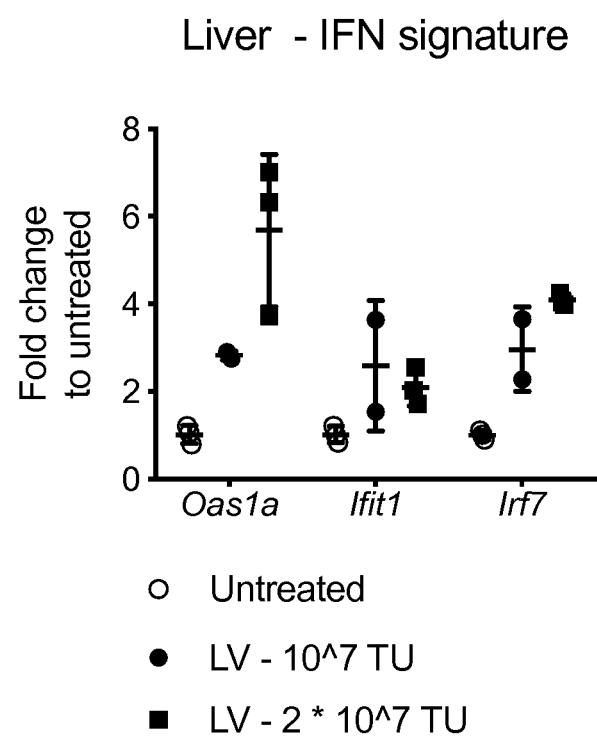

FIG. 6 LV-based delivery of interferon to the liver. Gene expression analysis by TaqMan showing the expression of a panel of genes in total liver from mice untreated or treated with the indicated doses of an LV-based IFNα release platform. Fold change vs. untreated.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

In one aspect the invention provides an enveloped viral particle producer or packaging cell, wherein the cell is genetically engineered to decrease expression of CD47 on the surface of the cell.

Decreased expression of CD47 on the surface of the cell refers to a decrease in the number of CD47 molecules that are expressed on the surface of the cell that has been genetically engineered, in comparison to the number of CD47 molecules that are expressed on the surface of a cell lacking the genetic engineering, but under otherwise substantially identical conditions.

The expression of CD47 on the surface of the cell may be decreased such that the number of surface-exposed CD47 molecules is, for example, less than about 50%, 40%, 30%, 25%, 20%, 15%, 10%, 5%, 4%, 3%, 2% or 1% of the number of surface-exposed CD47 molecules that are displayed in the absence of the genetic engineering. In one embodiment, the expression of CD47 on the surface of the cell is decreased such that the number of surface-exposed CD47 molecules is 0% of the number of surface-exposed CD47 molecules that are displayed in the absence of the genetic engineering.

The expression of CD47 on the surface of the cell is preferably decreased such that the cell is substantially devoid of surface-exposed CD47 molecules.

The term "substantially devoid" as used herein means that there is a substantial decrease in the number of CD47 molecules that are expressed on the surface of the cell that has been genetically engineered, in comparison to the number of CD47 molecules that are expressed on the surface of a cell lacking the genetic engineering (but under otherwise substantially identical conditions), such that enveloped viral particles produced by the cell exhibit a therapeutically useful increase in ability to transduce macrophages, phagocytes, antigen-presenting cells and/or monocytes, and/or induce a cytokine response upon systemic administration.

In another aspect the invention provides an enveloped viral particle producer or packaging cell, wherein the cell comprises a genetically engineered disruption of a gene encoding CD47.

In one embodiment, the cell is further genetically engineered to decrease expression of MHC-I on the surface of the cell.

In one embodiment, the cell further comprises a genetically engineered disruption of a gene encoding β2-microglobulin.

In one embodiment, the cell further comprises a genetically engineered disruption of one or more genes encoding an MHC-I α chain.

In one aspect, the invention provides a population of enveloped viral particle producer or packaging cells of the invention.

Preferably, at least about 50%, 60%, 70%, 75%, 80%, 85%, 90%, 95%, 96%, 97%, 98%, 99% or 100% of the cells in the population do not comprise surface-exposed CD47.

Preferably, at least about 50%, 60%, 70%, 75%, 80%, 85%, 90%, 95%, 96%, 97%, 98%, 99% or 100% of the cells in the population do not comprise surface-exposed MHC-I.

Methods for quantifying protein expression of cell surface-exposed proteins in a population of cells are known in the art. Suitable methods include flow cytometry, fluorescence-activated cell sorting (FACS) and fluorescence microscopy.

For example, a population of cells may be contacted with an antibody specific for CD47 or MHC-I. The antibody may be labelled to enable its detection. The antibody may be directly conjugated to a reporter moiety (e.g. a fluorescent label). Alternatively, a secondary antibody, conjugated to a reporter moiety and specific for the first antibody, may be contacted with the population of cells. Suitable reporter moieties are known in the art and include, for example, Alexa Fluor and BODIPY-based fluorescent labels. Once the population of cells has been contacted with the antibody, the population may be analysed using a technique suitable to allow quantification of protein expression on individual cells, such as flow cytometry. The analysis is carried out without lysing the cells.

The method for quantifying protein expression of cell surface-exposed proteins may also enable sorting of the population of cells to produce a population of cells enriched for a specific characteristic (e.g. to produce a population of cells enriched in cells that do not comprise surface-exposed CD47). For example, fluorescence-activated cell sorting (FACS) enables such enrichment to be performed.

Similar methods may be applied for quantifying protein expression of cell surface-exposed proteins on single cells. For example, the method may employ microfluidic approaches.

Cluster of Differentiation 47 (CD47)

Cluster of differentiation 47 (CD47; also known as integrin-associated protein, IAP) is a transmembrane protein belonging to the immunoglobulin superfamily. CD47 binds thrombospondin-1 (TSP-1) and signal-regulatory protein alpha (SIRPα), and functions as a signal to macrophages.

An example amino acid sequence of human CD47 is:

(SEQ ID NO: 1)
MWPLVAALLLGSACCGSAQLLENKTKSVEFTFCNDTVVIPCFVTNMEAQ

NTTEVYVKWKEKGRDIYTEDGALNKSTVPTDESSAKIEVSQLLKGDASL

KMDKSDAVSHTGNYTCEVTELTREGETIIELKYRVVSWESPNENILIVI

FPIFAILLFWGQFGIKTLKYRSGGMDEKTIALLVAGLVITVIVIVGAIL

FVPGEYSLKNATGLGLIVTSTGILILLHYYVFSTAIGLTSFVIAILVIQ

VIAYILAVVGLSLCIAACIPMHGPLLISGLSILALAQLLGLVYMKFVAS

NQKTIQPPRKAVEEPLNAFKESKGMMNDE

A further example amino acid sequence of human CD47 is:

(SEQ ID NO: 2)
MWPLVAALLLGSACCGSAQLLENKTKSVEFTFCNDTVVIPCFVTNMEAQ

NTTEVYVKWKFKGRDIYTEDGALNKSTVPTDESSAKIEVSQLLKGDASL

KMDKSDAVSHTGNYTCEVTELTREGETIIELKYRVVSWESPNENILIVI

FPIFAILLFWGQFGIKTLKYRSGGMDEKTIALLVAGLVITVIVIVGAIL

FVPGEYSLKNATGLGLIVTSTGILILLHYYVESTAIGLTSFVIAILVIQ

VIAYILAVVGLSLCIAACIPMHGPLLISGLSILALAQLLGLVYMKFV

A further example amino acid sequence of human CD47 is:

(SEQ ID NO: 3)
MWPLVAALLLGSACCGSAQLLENKTKSVEFTFCNDTVVIPCFVTNMEAQ

NTTEVYVKWKFKGRDIYTEDGALNKSTVPTDESSAKIEVSQLLKGDASL

KMDKSDAVSHTGNYTCEVTELTREGETIIELKYRVVSWESPNENILIVI

FPIFAILLFWGQFGIKTLKYRSGGMDEKTIALLVAGLVITVIVIVGAIL

FVPGEYSLKNATGLGLIVTSTGILILLHYYVFSTAIGLTSFVIAILVIQ

VIAYILAVVGLSLCIAACIPMHGPLLISGLSILALAQLLGLVYMKFVAS

NQKTIQPPRNN

A further example amino acid sequence of human CD47 is:

(SEQ ID NO: 4)
MWPLVAALLLGSACCGSAQLLENKTKSVEFTFCNDTVVIPCFVTNMEAQ

NTTEVYVKWKFKGRDIYTEDGALNKSTVPTDESSAKIEVSQLLKGDASL

KMDKSDAVSHTGNYTCEVTELTREGETIIELKYRVVSWESPNENILIVI

FPIFAILLFWGQFGIKTLKYRSGGMDEKTIALLVAGLVITVIVIVGAIL

FVPGEYSLKNATGLGLIVTSTGILILLHYYVFSTAIGLTSFVIAILVIQ

VIAYILAVVGLSLCIAACIPMHGPLLISGLSILALAQLLGLVYMKFVAS

NQKTIQPPRKAVEEPLN

An example nucleotide sequence encoding human CD47 is:

(SEQ ID NO: 5)
ATGTGGCCCCTGGTAGCGGCGCTGTTGCTGGGCTCGGCGTGCTGCGGAT

CAGCTCAGCTACTATTTAATAAAACAAAATCTGTAGAATTCACGTTTTG

TAATGACACTGTCGTCATTCCATGCTTTGTTACTAATATGGAGGCACAA

AACACTACTGAAGTATACGTAAAGTGGAAATTTAAAGGAAGAGATATTT

ACACCTTTGATGGAGCTCTAAACAAGTCCACTGTCCCCACTGACTTTAG

TAGTGCAAAAATTGAAGTCTCACAATTACTAAAAGGAGATGCCTCTTTG

AAGATGGATAAGAGTGATGCTGTCTCACACACAGGAAACTACACTTGTG

AAGTAACAGAATTAACCAGAGAAGGTGAAACGATCATCGAGCTAAAATA

TCGTGTTGTTTCATGGTTTTCTCCAAATGAAAATATTCTTATTGTTATT

TTCCCAATTTTTGCTATACTCCTGTTCTGGGGACAGTTTGGTATTAAAA

-continued

```
CACTTAAATATAGATCCGGTGGTATGGATGAGAAAACAATTGCTTTACT

TGTTGCTGGACTAGTGATCACTGTCATTGTCATTGTTGGAGCCATTCTT

TTCGTCCCAGGTGAATATTCATTAAAGAATGCTACTGGCCTTGGTTTAA

TTGTGACTTCTACAGGGATATTAATATTACTTCACTACTATGTGTTTAG

TACAGCGATTGGATTAACCTCCTTCGTCATTGCCATATTGGTTATTCAG

GTGATAGCCTATATCCTCGCTGTGGTTGGACTGAGTCTCTGTATTGCGG

CGTGTATACCAATGCATGGCCCTCTTCTGATTTCAGGTTTGAGTATCTT

AGCTCTAGCACAATTACTTGGACTAGTTTATATGAAATTTGTGGCTTCC

AATCAGAAGACTATACAACCTCCTAGGAAAGCTGTAGAGGAACCCCTTA

ATGCATTCAAAGAATCAAAAGGAATGATGAATGATGAATAA
```

Genetic Engineering of CD47

The enveloped viral particle producer or packaging cell of the invention is genetically engineered to decrease expression of CD47 on the surface of the cell.

Methods for genetic engineering to decrease protein expression are known in the art. For example, this may be achieved by targeted gene knockout. To decrease protein expression, the gene encoding the protein itself or its regulatory sequence (e.g. its promoter) may be knocked out. Knockout may be achieved by deletion of a section of the coding nucleic acid sequence, which may delete a section of the protein essential for expression or stability, or alter the reading frame of the coding sequence. Suitable methods for targeted gene knockout include use of zinc finger nucleases (ZFNs), transcription activator-like effector nucleases (TALENs) and CRISPR/Cas-based RNA-guided nucleases (Gaj, T. et al. (2013) Trends Biotechnol. 31:397-405).

For example, the CRISPR/Cas9 RNA-guided nuclease may be used to catalyse a double strand break at a specific locus in the genome if provided with appropriate RNA guides designed to bind that locus. Cas9 and the guide RNA may be delivered to a target cell by transfection of vectors encoding the protein and RNA. Cells attempt to repair any double strand breaks in their DNA using the non-homologous end joining (NHEJ) pathway. This is an error-prone mechanism which inserts random nucleotides and often disrupts the reading frame of the targeted gene.

Alternatively, the genetic engineering to decrease protein expression may be accomplished using RNAi techniques, or microRNA or antisense RNA to suppress expression of the target gene.

Once the targeted gene knockout or suppression of expression approach has been carried out, the resulting population of cells may be screened to select and enrich for those cells exhibiting the phenotype of interest, for example decreased expression of surface-exposed CD47. Suitable techniques for screening and enrichment are known in the art and include flow cytometry and fluorescence-activated cell sorting (FACS).

The cell may comprise genetically engineered disruptions in all copies of the gene encoding CD47.

Major Histocompatibility Complex Class I

The major histocompatibility complex class I (MHC-I) is a heterodimeric membrane protein that is displayed on the outer leaflet of the cell membrane (Penn, D. J. (2002) Major Histocompatibility Complex (MHC) eLS, John Wiley & Sons, http COLON SLASH SLASH www DOT els.net/ [DOI: 10.1038/npg.els.0000919]). MHC-I functions to bind and display peptide fragments of proteins to the extracellular environment where they may be recognised by CD8$^+$ cytotoxic T cells. Peptide fragments generated from normal cellular proteins will not activate cytotoxic T cells due to central and peripheral tolerance mechanisms. However, foreign peptides (e.g. those originating from viral proteins) will cause activation of an immune response to destroy the cell.

An allogeneic MHC-I protein itself may be recognised by the immune system. For example, antibodies may bind MHC-I epitopes directly. As a result, cells and enveloped viruses that comprise MHC-I proteins originating from an allogeneic source may be targeted and neutralised by the immune system.

Human MHC-I is also referred to as human leukocyte antigen class I (HLA-I) and is expressed on almost all nucleated cells. HLA-I consists of two polypeptide chains, an HLA-I heavy chain (α chain) and β2 microglobulin (β2M). The HLA-I α chain and β2M are linked non-covalently.

The HLA-I α chain is polymorphic. Six HLA-I α chains have been identified to date, including three classical, highly polymorphic α chains (HLA-A, HLA-B and HLA-C) and three non-classical, less polymorphic (HLA-E, HLA-F and HLA-G) α chains. The skilled person would readily be able to determine nucleic acid sequences of HLA-I α chains. For example, the HLA-I α chains may be identified in a genome sequence using their location within the major histocompatibility complex region of the chromosome (Penn, D. J. (2002) Major Histocompatibility Complex (MHC) eLS, John Wiley & Sons, http COLON SLASH SLASH www DOT els.net/[DOI: 10.1038/npg.els.0000919]).

Nucleic acid sequences encoding β2M are known in the art. For example, a nucleic acid sequence of human B2M is deposited as GenBank Accession No. NM_004048.

The skilled person will understand that the present invention is applicable to variants of MHC-I sequences, such as polymorphisms of these sequences (e.g. HLA-I α chain sequences and β2M sequences). For example, variants of MHC-I sequences may include single nucleotide polymorphisms (SNPs) or multiple SNPs.

In one embodiment, the enveloped viral particle producer or packaging cell comprises a genetically engineered disruption of a gene encoding β2-microglobulin. β2-microglobulin stabilises MHC-I, thus cells deficient in β2-microglobulin will exhibit decreased expression of MHC-I on the surface of the cell. The cell may comprise genetically engineered disruptions in all copies of the gene encoding β2-microglobulin.

In another embodiment, the cell comprises a genetically engineered disruption of a gene encoding an MHC-I α chain. The cell may comprise genetically engineered disruptions in all copies of the gene encoding an MHC-I α chain.

The cell may comprise both genetically engineered disruptions of genes encoding β2-microglobulin and genetically engineered disruptions of genes encoding an MHC-I α chain.

Vectors

A vector is a tool that allows or facilitates the transfer of an entity from one environment to another. The viral particles of the present invention may be vectors.

The viral vector particles of the invention are enveloped viral particles.

An enveloped viral particle comprises an outer lipid bilayer membrane. Numerous enveloped viruses are known in the art, including retrovirus, herpes simplex virus, vaccinia virus, hepadnavirus, togavirus, flavivirus, arenavirus, coronavirus, orthomyxovirus, paramyxovirus, bunyavirus, bornavirus, rhabdovirus and filovirus.

The enveloped viral particle of the invention may be, for example, a retroviral, herpes simplex viral, vaccinia viral, hepadnaviral, togaviral, flaviviral, arenaviral, coronaviral, orthomyxoviral, paramyxoviral, bunyaviral, bornaviral, rhabdoviral or filoviral particle, or a viral particle derived therefrom. The term "derived from" as used herein may refer to, for example, the incorporation of at least one component part derivable from a certain type of virus.

Retroviral and Lentiviral Vectors

A retroviral vector may be derived from or may be derivable from any suitable retrovirus. A large number of different retroviruses have been identified. Examples include murine leukaemia virus (MLV), human T-cell leukaemia virus (HTLV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), avian myelocytomatosis virus-29 (MC29) and avian erythroblastosis virus (AEV). A detailed list of retroviruses may be found in Coffin, J. M. et al. (1997) Retroviruses, Cold Spring Harbour Laboratory Press, 758-63.

Retroviruses may be broadly divided into two categories, "simple" and "complex". Retroviruses may be even further divided into seven groups. Five of these groups represent retroviruses with oncogenic potential. The remaining two groups are the lentiviruses and the spumaviruses. A review of these retroviruses is presented in Coffin, J. M. et al. (1997) Retroviruses, Cold Spring Harbour Laboratory Press, 758-63.

The basic structure of retrovirus and lentivirus genomes share many common features such as a 5' Long Terminal Repeats (LTR) and a 3' LTR. Between or within these are located a packaging signal to enable the genome to be packaged, a primer binding site, integration sites to enable integration into a host cell genome, and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called LTRs. The LTRs are responsible for proviral integration and transcription. LTRs also serve as enhancer-promoter sequences and can control the expression of the viral genes.

The LTRs themselves are identical sequences that can be divided into three elements: U3, R and U5. U3 is derived from the sequence unique to the 3' end of the RNA. R is derived from a sequence repeated at both ends of the RNA. U5 is derived from the sequence unique to the 5' end of the RNA. The sizes of the three elements can vary considerably among different retroviruses.

In a defective retroviral vector genome gag, pol and env may be absent or not functional.

In a typical retroviral vector, at least part of one or more protein coding regions essential for replication may be removed from the virus. This makes the viral vector replication-defective. Portions of the viral genome may also be replaced by a library encoding candidate modulating moieties operably linked to a regulatory control region and a reporter moiety in the vector genome in order to generate a vector comprising candidate modulating moieties which is capable of transducing a target host cell and/or integrating its genome into a host genome.

Lentivirus vectors are part of the larger group of retroviral vectors. A detailed list of lentiviruses may be found in Coffin, J. M. et al. (1997) Retroviruses, Cold Spring Harbour Laboratory Press, 758-63. Briefly, lentiviruses can be divided into primate and non-primate groups. Examples of primate lentiviruses include but are not limited to human immunodeficiency virus (HIV), the causative agent of human acquired immunodeficiency syndrome (AIDS); and simian immunodeficiency virus (SIV). Examples of non-primate lentiviruses include the prototype "slow virus" visna/maedi virus (VMV), as well as the related caprine arthritis-encephalitis virus (CAEV), equine infectious anaemia virus (EIAV), and the more recently described feline immunodeficiency virus (FIV) and bovine immunodeficiency virus (BIV).

The lentivirus family differs from retroviruses in that lentiviruses have the capability to infect both dividing and non-dividing cells (Lewis, P et al. (1992) EMBO J. 11:3053-8; Lewis, P. F. et al. (1994) J. Virol. 68:510-6). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "primate" vector. The lentiviral vector may be a "non-primate" vector (i.e. derived from a virus which does not primarily infect primates, especially humans). Examples of non-primate lentiviruses may be any member of the family of lentiviridae which does not naturally infect a primate.

As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat.

Most HIV-2-based vectors are structurally very similar to HIV-1 vectors. Similar to HIV-1-based vectors, HIV-2 vectors also require RRE for efficient transport of the full-length or singly spliced viral RNAs.

In one system, the vector and helper constructs are from two different viruses, and the reduced nucleotide homology may decrease the probability of recombination. In addition to vectors based on the primate lentiviruses, vectors based on FIV have also been developed as an alternative to vectors derived from the pathogenic HIV-1 genome. The structures of these vectors are also similar to the HIV-1 based vectors.

Preferably the viral vector used in the present invention has a minimal viral genome.

By "minimal viral genome" it is to be understood that the viral vector has been manipulated so as to remove the non-essential elements and to retain the essential elements in order to provide the required functionality to infect, transduce and deliver a nucleotide sequence of interest to a target host cell. Further details of this strategy can be found in WO 1998/017815.

Preferably the plasmid vector used to produce the viral genome within a host cell/packaging cell will have sufficient lentiviral genetic information to allow packaging of an RNA genome, in the presence of packaging components, into a viral particle which is capable of infecting a target cell, but is incapable of independent replication to produce infectious viral particles within the final target cell. Preferably the vector lacks a functional gag-pol and/or env gene and/or other genes essential for replication.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed viral sequence (i.e. the 5' U3 region), or they may be a heterologous promoter, such as another viral promoter (e.g. the CMV promoter).

The vectors may be self-inactivating (SIN) vectors in which the viral enhancer and promoter sequences have been deleted. SIN vectors can be generated and transduce non-dividing cells in vivo with an efficacy similar to that of wild-type vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

The vectors may be integration-defective. Integration defective lentiviral vectors (IDLVs) can be produced, for example, either by packaging the vector with catalytically inactive integrase (such as an HIV integrase bearing the D64V mutation in the catalytic site; Naldini, L. et al. (1996) Science 272:263-7; Naldini, L. et al. (1996) Proc. Natl. Acad. Sci. USA 93:11382-8; Leavitt, A. D. et al. (1996) J. Virol. 70:721-8) or by modifying or deleting essential att sequences from the vector LTR (Nightingale, S. J. et al. (2006) Mol. Ther. 13:1121-32), or by a combination of the above.

HIV-Derived Vectors

HIV-derived vectors for use in the present invention are not particularly limited in terms of HIV strain. Numerous examples of sequences of HIV strains may be found at the HIV Sequence Database (http COLON SLASH SLASH www DOT hiv.lanl.gov/content/index).

Herpes Simplex Virus (HSV) Derived Vectors

Herpes simplex virus (HSV) is an enveloped double-stranded DNA virus that naturally infects neurons. HSV can accommodate large sections of foreign DNA, which makes it attractive as a vector system, and has been employed as a vector for gene delivery to neurons.

The use of HSV in therapeutic procedures requires the strains to be attenuated so that they cannot establish a lytic cycle. In particular, if HSV vectors are to be used for gene therapy in humans, the NOI is preferably inserted into an essential gene. This is necessary, because if a vector virus encounters a wild type virus, transfer of a heterologous gene to the wild type virus could occur by recombination. However, as long as the NOI is inserted into an essential gene, recombinational transfer would also delete the essential gene in the recipient virus and prevent "escape" of the heterologous gene into the replication competent wild type virus population.

Vaccinia Virus-Derived Vectors

Vaccinia virus is large enveloped virus that has an approximately 190 kb linear, double-stranded DNA genome. Vaccinia virus can accommodate up to approximately 25 kb of foreign DNA, which also makes it useful for the delivery of large genes.

A number of attenuated vaccinia virus strains are known in the art that are suitable for gene therapy applications, for example the MVA and NYVAC strains.

Viral Particle Production

In one aspect, the invention provides the use of the enveloped viral particle producer cell of the invention for the production of enveloped viral particles.

In one embodiment, the enveloped viral particles each comprise less than 10, 5, 4, 3, 2 or 1 surface-exposed CD47 molecules.

In one embodiment, the enveloped viral particles each comprise less than 10 surface-exposed CD47 molecules. In one embodiment, the enveloped viral particles each comprise less than 5 surface-exposed CD47 molecules. In one embodiment, the enveloped viral particles each comprise less than 2 surface-exposed CD47 molecules.

In one embodiment, the enveloped viral particles do not comprise any surface-exposed CD47 molecules.

In one embodiment, the enveloped viral vector particles comprise less than about 50%, 40%, 30%, 25%, 20%, 15%, 10%, 5%, 4%, 3%, 2% or 1% of the number of surface-exposed CD47 molecules that are displayed on particles produced by enveloped viral particle producer cells in the absence of the genetic engineering (but under otherwise substantially identical conditions). In another embodiment, the enveloped viral particles are substantially devoid of surface-exposed CD47 molecules.

In one embodiment, the enveloped viral vector particles comprise less than about 50%, 40%, 30%, 25%, 20%, 15%, 10%, 5%, 4%, 3%, 2% or 1% of the number of surface-exposed MHC-I molecules that are displayed on particles produced by enveloped viral particle producer cells in the absence of the genetic engineering (but under otherwise substantially identical conditions). In another embodiment, the enveloped viral particles are substantially devoid of surface-exposed MHC-I molecules.

Methods for quantifying the number of surface-exposed proteins on viral particles are known in the art. Suitable methods include electron microscopy.

For example, a sample of viral particles may be adsorbed onto electron microscopy grids (e.g. as disclosed in the Examples) and fixed thereon using paraformaldehyde. The samples may then be incubated first with a primary antibody specific for the protein of interest (e.g. CD47), and then with a gold particle-conjugated secondary antibody specific for the primary antibody, before a further fixing step using paraformaldehyde. The sample may then be visualised using an electron microscope and the gold particles counted to allow quantification of the number of surface-exposed proteins of interest.

The enveloped viral particle producer cell may comprise the viral genome.

The viral genome is the nucleic acid sequence that is incorporated into the viral particle. The viral genome may be engineered to comprise a nucleotide of interest (NOI).

Accordingly, for use in producing viral particles, the enveloped viral particle producer cell may comprise the viral genome and subsequently cultured under conditions suitable for the production of the enveloped viral particles.

An "enveloped viral particle packaging cell" may, for example, comprise nucleic acid sequences encoding some or all the structural proteins required for viral particle assembly.

Cells comprising only some of the elements required for the production of enveloped viral particles are useful as intermediate reagents in the generation of viral particle producer cell lines, through subsequent steps of transient transfection, transduction or stable integration of each additional required element. These intermediate reagents are encompassed by the packaging cell lines of the invention. Parental cells to be subsequently used for the generation of enveloped viral particle producer or packaging cell lines, in which the expression of CD47 on the surface of the cell has been decreased represent another embodiment of the invention.

The nucleic acid sequences encoding the components required for production of an infectious enveloped viral particle may be transiently transfected or transduced into or stably maintained (e.g. stably integrated into the cell genome or episomally maintained) within the packaging or producer cell. Alternatively, a combination of transient transfection or transduction and stable maintenance may be used to introduce the nucleic acid sequences into the cell.

Accordingly, the cell of the invention may be transfected or transduced with or engineered to stably integrate by targeted integration a nucleic acid comprising the viral genome to enable production of enveloped viral particles which comprise the viral genome.

The nucleic acid sequences encoding separate components required for production of an infectious enveloped viral particle may be provided to the cell as separate expression cassettes.

In one embodiment, the packaging cell of the invention comprises nucleic acid sequences encoding Gag, Gag/Pol, and/or Env proteins, or functional substitutes thereof. The cell may optionally comprise nucleic acid sequences encoding additional proteins that may be required for retroviral vector particle assembly, for example Rev protein.

Enveloped viral particle producer or packaging cells can be of any suitable cell type that is capable of producing or packaging enveloped viral particles. The cells are preferably mammalian cells, particularly human cells. For example, the enveloped viral particles producer cell may be derived from a parental HEK-293 cell.

Nucleotide of Interest

The viral particles of the invention may comprise a nucleotide of interest (NOI).

Preferably, the nucleotide of interest gives rise to a therapeutic effect.

Suitable NOIs include, but are not limited to sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, ribozymes, miRNA target sequences, a transdomain negative mutant of a target protein, toxins, conditional toxins, antigens, viral proteins, bacterial proteins, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group). The NOIs may also encode pro-drug activating enzymes.

In one embodiment, the enveloped viral particle comprises a transgene encoding a cytokine. In one embodiment, the enveloped viral particle comprises a transgene encoding interferon, preferably interferon-α. The invention may enable delivery of one or more cytokines to liver macrophages for the treatment or prevention of cancer, such as metastasis. The invention may enable delivery of interferon (e.g. interferon-α) to the liver, e.g. to liver macrophages.

A further example of a NOI is the coagulation factor VIII or factor IX or engineered derivatives thereof, which may be used for gene therapy of haemophilia or the beta-globin chain which may be used for gene therapy of thalassemia/sickle cell disease.

Suitable proteins that can be transferred by viral vector protein transfer include, but are not limited to nucleases, integrases, transposases, enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, a transdomain negative mutant of a target protein, toxins, conditional toxins, antigens, viral proteins, bacterial proteins, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group).

Pharmaceutical Composition

The enveloped viral particles or transduced cells of the invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy products is preferably performed in compliance with FACT-JACIE International Standards for cellular therapy.

Gene Therapy

In one aspect, the invention provides enveloped viral particles and transduced cells for use in therapy, for example for use in gene therapy. The enveloped viral particles may be referred to as enveloped viral vector particles.

By a "transduced cell" or a cell which has been "transduced by an enveloped viral vector particle", it is to be understood that the nucleic acid (e.g. comprising the NOI) carried by the enveloped viral vector particle has been transferred to the cell. The cell to be transduced is preferably a target cell.

The enveloped viral vector particles of the invention may be administered directly to a subject (e.g. systemically). The viral vector particles may be engineered to target infection to specific cells in a subject. The viral vector particles may also be engineered to target expression of the NOI to specific cells in a subject. This may be achieved using tissue-specific promoters or nucleic acid sequences which facilitate suppression of NOI expression in specific cells.

The enveloped viral vector particles may also be used to transduce cells that have been removed from the body of a subject as part of an ex vivo gene therapy approach.

The transduced cells may be administered as part of an autologous cell transplant procedure or as part of an allogeneic cell transplant procedure.

By "autologous cell transplant procedure" it is to be understood that the starting population of cells (which are then transduced with the enveloped viral vector particles of the invention) is obtained from the same subject as that to which the transduced cell population is administered. Autologous transplant procedures are advantageous as they avoid problems associated with immunological incompatibility and are available to subjects irrespective of the availability of a genetically matched donor.

By "allogeneic cell transplant procedure" it is to be understood that the starting population of cells (which are then transduced with the enveloped viral vector particles of the invention) is obtained from a different subject as that to which the transduced cell population is administered. Preferably, the donor will be genetically matched to the subject to which the cells are administered to minimise the risk of immunological incompatibility.

Suitable doses of the enveloped viral vector particles or transduced cells are such as to be therapeutically and/or prophylactically effective. The dose to be administered may depend on the subject and condition to be treated, and may be readily determined by a skilled person.

The viral vector particles of the invention are able to transduce professional phagocytes and antigen-presenting cells (APCs) with higher efficiency than viral particles that do not exhibit decreased levels of surface-exposed CD47.

The viral vector particles of the invention may be used to transfer transgenes into cells such as phagocytes and APCs. The viral vector particles may be used for the treatment of cancer, for example by cancer immunotherapy or through direct anti-tumour effects. In addition, the viral vector particles may be used to treat infections, immune-mediated diseases or autoimmune diseases. These effects may be achieved through the transfer of transgenes into APCs.

The viral vector particles of the invention may be used to transfer antigens into APCs for immunisation (vaccination) or immune-modulation purposes.

The viral vector particles of the invention may also be used for targeting macrophages. In one aspect, the invention provides use of an enveloped viral particle of the invention for transducing a liver macrophage. Preferably, the enveloped viral particle comprises a transgene encoding a cytokine In another aspect, the invention provides the enveloped viral particle or transduced cell of the invention for use in the treatment or prevention of cancer, preferably liver cancer (e.g. liver metastasis). Preferably, the enveloped viral particle comprises a transgene encoding a cytokine.

The enveloped viral vector particle or transduced cells of the invention may be useful in the treatment of genetic diseases, such as plasma protein deficiencies, metabolic disorders, lysosomal storage disorders, mucopolysaccharidoses, immune deficiencies, haematological disorders, including but not limited to haemophilia, adenosine deaminase severe combined Immunodeficiency, Wiskott-Aldrich syndrome, metachromatic leukodystrophy, globoid leukodystrophy, β-thalassemia and chronic granulomatous disease.

The enveloped viral vector particles or transduced cells of the invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis;

tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the enveloped viral vector particles or transduced cells of the invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the enveloped viral vector particles or transduced cells of the invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Method of Treatment

It is to be appreciated that all references herein to treatment include curative, palliative and prophylactic treatment, although in the context of the present invention references to preventing are more commonly associated with prophylactic treatment. The treatment of mammals, particularly humans, is preferred. Both human and veterinary treatments are within the scope of the present invention.

Vaccines

In one aspect, the invention provides an enveloped viral particle of the invention for use as a vaccine. Preferably the enveloped viral particle is not infectious, for example is incapable of infecting a cell. Preferably, the enveloped viral particle is incapable of replication.

Attenuated viruses are commonly used in the art as vaccines to provide immunity against infection by the natural, virulent forms of the viruses.

Attenuated viruses for use as vaccines may be produced using the producer cells of the invention as described above, preferably wherein the NOI may be omitted. The producer cells of the invention enable the production of enveloped viral particles that exhibit decreased numbers of surface-exposed CD47 molecules for use as vaccines. The enveloped viral vector particle for use as a vaccine may be substantially devoid of surface-exposed CD47 molecules.

In one embodiment, the enveloped viral particles for use as a vaccine each comprise less than 10, 5, 4, 3, 2 or 1 surface-exposed CD47 molecules.

In one embodiment, the enveloped viral particles for use as a vaccine each comprise less than 10 surface-exposed CD47 molecules. In one embodiment, the enveloped viral particles for use as a vaccine each comprise less than 5 surface-exposed CD47 molecules. In one embodiment, the enveloped viral particles for use as a vaccine each comprise less than 2 surface-exposed CD47 molecules.

In one embodiment, the enveloped viral particles for use as a vaccine each comprise less than about 50%, 40%, 30%, 25%, 20%, 15%, 10%, 5%, 4%, 3%, 2% or 1% of the number of surface-exposed CD47 molecules that are displayed on particles produced by enveloped viral particle producer cells in the absence of the genetic engineering (but under otherwise substantially identical conditions).

In one embodiment, the enveloped viral particles for use as a vaccine do not comprise any surface-exposed CD47 molecules.

The producer cells of the invention may also enable the production of enveloped viral particles that exhibit decreased numbers of surface-exposed MHC-I molecules for use as vaccines. The enveloped viral vector particle for use as a vaccine may be substantially devoid of surface-exposed MHC-I molecules.

A decreased number or lack of surface-exposed MHC-I molecules is advantageous in viruses for use as vaccines, as the viruses will be less likely to be neutralised by antibodies binding to MHC-I.

Additionally, the immune response may react against the allogeneic MHC-I rather than against viral antigens, therefore viral particles substantially devoid of allogeneic MHC-I molecules may be more effective vaccines, by more effectively inducing protective immunity.

The viruses for use as vaccines may be further engineered to express additional proteins on their surfaces or within infected cells. Such proteins may act as antigens for the generation of antibodies or cellular immunity which may further increase the body's immune defences.

In one embodiment, the enveloped viral particles further comprise one or more antigens. The one or more antigens may be derived, for example, from a virus, bacterium, fungus, protozoan and/or parasite.

In one embodiment, the antigen is derived from a virus selected from the group consisting of Ebola, herpes simplex virus, varicella zoster virus, Epstein-Barr virus, cytomegalovirus, hepatitis A virus, hepatitis B virus, hepatitis C virus, delta hepatitis virus, hepatitis E virus, hepatitis G virus, Picornaviridae (e.g. polioviruses), Caliciviridae, Togaviridae (e.g. rubella virus and dengue virus), Flaviviridae, Coronaviridae, Reoviridae, Birnaviridae, Rhabodoviridae (e.g. rabies virus), Filoviridae, Paramyxoviridae (e.g. mumps virus, measles virus and respiratory syncytial virus), Orthomyxoviridae (e.g. influenza virus types A, B and C), Bunyaviridae, Arenaviridae and Retroviradae (e.g. HIV-1, HIV-2 and SIV).

In one embodiment, the antigen is derived from a bacterium that is causative of diphtheria, tetanus, pertussis or meningitis.

In one embodiment, the antigen is derived from a bacteria selected from the group consisting of *Corynebacterium diphtheriae, Clostridium tetani, Bordetella pertusis, Neisseria meningitidis*, including serotypes Meningococcus A, B, C, Y and WI35 (MenA, B, C, Y and WI35), *Haemophilus* influenza type B (Hib) and *Helicobacter pylori.*

In one embodiment, the antigen is derived from a parasite that is causative of malaria or Lyme disease.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

Results

CD47 Disruption in Producer Cells does not Affect Lentivirus (LV) Production

Figure 1:
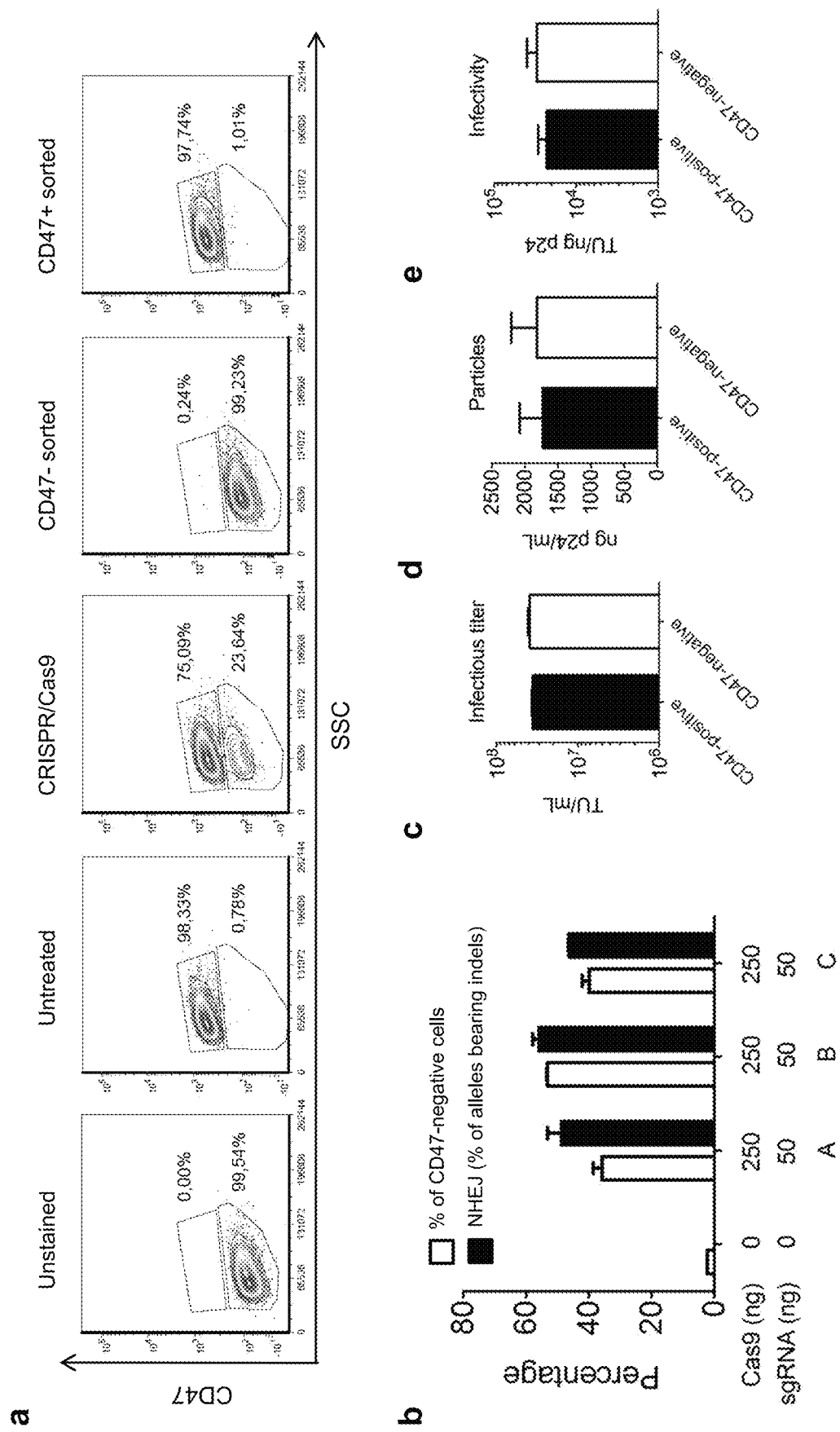
FIG. 1 Generation and characterisation of CD47-negative producer cells. (a) Flow cytometry analysis (contour plots with outliers) of 293T cells unstained, untreated, CRISPR/Cas9 treated, CD47-negative or CD47-positive sorted (as indicated) performed 3 days after sorting. (b) Percentage of CD47-negative cells (white bars) and of alleles bearing indels (NHEJ, black bars) in 293T cells transiently transfected with the 3 different sgRNAs (A, B or C) with the indicated quantities of Cas9 and sgRNA expressing plasmids, 1 week after transfection. (c-e) Mean with SEM of (c)

CD47 is a known inhibitor of phagocytosis through the species-specific interaction with its receptor, the SIRPα receptor. In order to obtain lentivirus (LV) devoid of CD47 molecules on their surface (CD47-free LV), we genetically inactivated CD47 gene in producer cells by transient transfection of a Cas9 expressing plasmid together with three different gRNAs and FACS-sorted to purity CD47-negative producer cells (FIG. 1 a-b). CD47-negative cells produced LV with equivalent infectivity as their CD47-positive counterpart (FIG. 1c).

CD47-Free LV Show Enhanced Transduction of Primary Human Phagocytes

CD47 molecules are incorporated on LV particles at levels proportional to CD47 expression on producer cell membrane as shown by electron microscopy of LV particles immunostained with anti-CD47 antibodies (FIG. 2a, b). Thus, LV produced by CD47-negative cells are CD47-free LV. Importantly, the CD47 content on LV particles did not affect envelope VSV.G protein incorporation (FIG. 2c). When matched input of CD47-free and control LV were exposed to primary human macrophages, we found a significantly higher transduction by the former than the latter of human macrophages, while transduction of reference 293T cells remained unchanged (FIG. 2d). These data indicate that modulating the levels of CD47 on LV particles affect their uptake by human macrophages. We transduced human primary monocytes with LV-GFP at day 2 of dendritic cell differentiation protocol, measured GFP expression at the end of differentiation and found higher gene transfer efficiency by CD47-free LV than control LV (FIG. 2e). In addition, we generated fluorescent LV, carrying green fluorescent protein (GFP) fused to the membrane-targeting domain of pp60Src, a chimeric protein previously shown to be effectively incorporated in the budding HIV envelope. These fluorescent LV particles can be visualised post-entry in primary human macrophages using ImageStream, a combined flow cytometry and imaging system that allows high-throughput quantification of LV entry. Using this approach we confirmed the increased phagocytosis of CD47-free LV compared to control LV (FIG. 2f).

CD47-Free LV Show Increased Uptake by Liver and Spleen Professional Phagocytes when Administered In Vivo It has been shown that SIRPα of non-obese diabetic (NOD) mice has high affinity for human CD47. We thus compared the outcome of LV administration to NOD and C57BL/6 haemophilia B mice. We found 4-fold higher LV copies per cell (vector copy number, VCN) in sorted hepatocytes and 30- and 5-fold lower VCN in liver macrophages and spleen, respectively, in NOD versus C57BL/6 mice (FIG. 3a). Interestingly, LV copies were also >10-fold lower in NOD plasmacytoid dendritic cells (pDC), which are known sensors of viral nucleic acid and were reported to release type-I interferon (IFN) after exposure to LV particles. These inter-strain differences in biodistribution among liver cell types were primarily dependent on the interaction between the NOD SIRP-α and the human CD47 molecule on LV particles, because they were almost completely abrogated when we administered at the same dose CD47-free LV (FIG. 3b). CD47-free LV transduced liver macrophages, liver pDC and spleen at higher efficiency than its CD47-bearing counterparts in NOD mice (FIG. 3c).

CD47-Free LV Administration Caused an Increase in Phagocyte-Related Pro-Inflammatory Cytokines Surface display of CD47 also affected the acute cytokine and chemokine release, following intravenous LV administration. Specifically, Interleukine-6 (IL6), monocyte chemoattractant protein 1 (MCP-1), macrophage inflammatory protein 1 (MIP-1α), MIP-1β, chemokine (C-X-C motif) ligand 1 (CXCL1) and granulocyte-colony stimulating factor (G-CSF) significantly increased in LV-treated compared to untreated NOD mice, 3 hours after LV administration. Interestingly, the administration of CD47-free LV to NOD mice triggered the strongest increase in these macrophage-related and pro-inflammatory cytokines (FIG. 4 a-l). These data are in line with the observed modulation of professional phagocytes' uptake by the CD47 content of the LV particles.

Intravital Imaging Shows that CD47 Regulates the Rate and Extent of LV Phagocytosis by Kupffer Cells (KC)

To investigate the kinetics of LV phagocytosis in the liver in real time upon intravenous administration, we performed intravital two-photon microscopy (IV2PM). To visualise LV we used fluorescent LV produced in control 293T, CD47hi 293T or CD47-negative 293T cells, as described herein. LV uptake was recorded live in the surgically exposed liver of anesthetised mice. Administration of GFP-labelled LV in C57BL/6 mice resulted in rapid and widespread uptake by Kupffer cells (KC) (visualised by anti-F4/80 antibody infusion prior to LV administration), which became all LV-positive in the examined field within 5-10 minutes upon administration (FIG. 5). By contrast, administration of the same LV into NOD mice showed a delayed and overall decreased uptake by KC; this was even further reduced when CD47hi LV were administered, with only half the fraction of LV-positive KC at the end of recording (40 minutes post LV) for CD47hi compared to control LV. Importantly, the kinetics and amount of CD47-free LV uptake by KC in NOD mice were instead very fast and overlapping with those of control LV injected in C57BL/6 mice. The remarkably different timing and extent of LV uptake by KC according to the recognition and content of CD47 on the LV surface provides direct evidence of a major role of this molecule in shielding LV from phagocytosis in vivo.

LV-Based Delivery of Interferon to the Liver

Our results indicate that LV-based delivery of interferon alpha (IFNα) induces the activation of an IFN signature in the liver of treated mice (FIG. 6). Of note, the rationale for exploiting the in vivo gene therapy above-described, rather than relying on exogenous cytokine administration, is based on the opportunity to spare off-target tissues and reach local, stable and continuous cytokine expression at near physiological levels, thus limiting the risk of (i) adverse events; (ii) off-target effects; and (iii) desensitisation from exposure to excessive cytokine dosing. Our scaled-up studies in non-human primates (NHP) indicate that stable, robust and hepatic LV-driven transgene expression is attainable without any significant acute toxicity and with recovery of nearly all integrated LVs from the liver and spleen (Milani et al. (2019) Sci Transl Med).

Materials and Methods

Plasmid Construction

The Cas9 and sgRNA expressing plasmids were previously described (Amabile, A. et al. (2016) Cell 167:219-232 e214). The sequences of the CRISPR used to generate the sgRNA are: CD47 A (CTACTGAAGTATACGTAAAGTGG) (SEQ ID NO: 6); B (CTTGTTTAGAGCTCCATCAAAGG) (SEQ ID NO: 7); and C (ATCGAGCTAAAATATCGTGTTGG) (SEQ ID NO: 8).

Vector Production

Lab-grade VSV.G-pseudotyped third-generation self-inactivating (SIN) LV were produced by calcium phosphate transient transfection into 293T cells, or by LV stable producer cell lines (Milani et al., EMBO Mol Med 9 (11): 1558-1573). 293T cells were transfected with a solution containing a mix of the selected LV genome transfer plasmid, the packaging plasmids pMDLg/pRRE and pCMV.REV, pMD2.G and pAdvantage, as previously described (Milani et al., EMBO Mol Med 9 (11): 1558-1573). Medium was changed 14-16 hours after transfection and supernatant was collected 30 hours after medium change. Alternatively, LV production was induced when LV producer cells were in a sub-confluent state, by replacing the culture medium with medium containing doxycycline (Sigma) 1 µg/mL and supernatant was collected 3 days after induction. LV-containing supernatants were sterilised through a 0.22 µm filter (Millipore) and, when needed, transferred into sterile poliallomer tubes (Beckman) and centrifuged at 20,000 g for 120 min at 20° C. (Beckman Optima XL-100K Ultracentrifuge). LV pellet was dissolved in the appropriate volume of PBS to allow 500-1000× concentration.

LV Titration

For LV titration, $1 \times 10^5$ 293T cells were transduced with serial LV dilutions in the presence of polybrene (8 µg/mL). For LV-GFP, cells were analysed by flow cytometry 3-7 days after transduction and infectious titre, expressed as transducing units 293T (TU)/mL, was calculated using the formula TU/mL=((% GFP+ cells/100)×100,000× (1/dilution factor)). For all other LV, genomic DNA (gDNA) was extracted 14 days after transduction, using Maxwell 16 Cell DNA Purification Kit (Promega), following the manufacturer's instructions. VCN was determined by quantitative PCR (qPCR) starting from 100 ng of template gDNA using primers (HIV fw: 5'-TACTGACGCTCTCGCACC-3' (SEQ ID NO: 9); HIV rv: 5'-TCTCGACGCAGGACTCG-3' (SEQ ID NO: 10)) and a probe (FAM 5'-ATCTCTCTCCTTCTAGCCTC-3' (SEQ ID NO: 11)) designed on the primer binding site region of LV. The amount of endogenous DNA was quantified by a primers/probe set designed on the human telomerase gene (Telo fw: 5'-GGCACACGTGGCTTTTCG-3' (SEQ ID NO: 12); Telo rv: 5'-GGTGAACCTCGTAAGTTTATGCAA-3' (SEQ ID NO: 13); Telo probe: VIC 5'-TCAGGACGTCGAGTGGACACGGTG-3' (SEQ ID NO: 14) TAMRA) or the human GAPDH gene (Applied Biosystems HS00483111_cm). VCN was calculated by the formula=(ng LV/ng endogenous DNA)×VCN of sample used for the standard curve. The standard curve was generated, by using a CEM cell line stably carrying 1 vector integrant, which was previously determined by Southern blot and fluorescent in situ hybridisation (FISH). All reactions were carried out in duplicate or triplicate in a Viia7 Real Time PCR thermal cycler (Applied Biosystems). Each qPCR run carried an internal control generated by using a CEM cell line stably carrying 4 vector integrants, which were previously determined by Southern blot and FISH analysis. Infectious titre, expressed as TU/mL, was calculated using the formula TU/mL=(VCN×100,000× (1/dilution factor). LV physical particles were measured by HIV-1 Gag p24 antigen immunocapture assay (Perkin Elmer) following the manufacturer's instructions. LV specific infectivity was calculated as the ratio between infectious titre and physical particles.

Mice Experiments

NOD and wild-type C57BL/6 mice were purchased from Charles River. All mice were maintained in specific pathogen-free conditions. Vector administration was carried out in adult (7-10 week old) mice by tail-vein injection. Mice were bled from the retro-orbital plexus using capillary tubes and blood was collected into 0.38% sodium citrate buffer, pH 7.4. Mice were deeply anesthetised with tribromoethanol (Avertin) and euthanised by $CO_2$ inhalation at the scheduled times. All animal procedures were performed according to protocols approved by the Institutional Animal Care and Use Committee.

Fractionation and Sorting of Liver Cell Sub-Populations

The liver was perfused (2.5 mL/min) via the inferior vena cava with 12.5 mL of the following solutions at subsequent steps: 1) PBS EDTA (0.5 mM), 2) HBSS (Hank's balanced salt solution, Gibco) and HEPES (10 mM), 3) HBSS-HEPES 0.03% Collagenase IV (Sigma). The digested liver tissue was harvested, passed through a 70 µm cell strainer (BD Biosciences) and processed into a single-cell suspension. This suspension was subsequently centrifuged three times (30, 25 and 20 g, for 3 minutes, at room temperature) to obtain PC-containing pellets. The nPC-containing supernatant was centrifuged (650 g, 7 minutes, at room temperature) and recovered cells were loaded onto a 30/60% Percoll (Sigma) gradient (1800 g, for 20 minutes at room temperature). nPC interface was collected and washed twice. The nPC were subsequently incubated with the following monoclonal antibodies: e-fluor 450-conjugated anti-CD45 (30-F11, e-Bioscience), Allophycocyanin (APC)-conjugated anti-CD31 (MEC13.3, BD Biosciences), phycoerythrin (PE)-conjugated F4/80 (CI: A3-1, Biorad), PE-Cy5-conjugated anti-CD45R/B220 (from BD Biosciences), PE-Cy7-conjugated anti-CD11c (N418, e-Bioscience), purified anti-CD16/32 (2.4G2, BD Biosciences). nPC subpopulations (LSEC, KC, pDC) were sorted by FACS, MOFLO-DAKO- Beckman-Coulter; the nPC contaminating the PC suspension, were removed by FACS excluding cells labelled by APC-conjugated anti-CD31/anti-CD45 cocktail, thus obtaining sorted hepatocytes (Hep).

Cell Cultures and In Vitro Experiments 293T and LV producer cell lines were maintained in Iscove's modified Dulbecco's medium (IMDM, Sigma) supplemented with 10% foetal bovine serum (FBS, Euroclone), 4 mM glutamine (Lonza), penicillin and streptomycin 100 IU/mL (Lonza). Primary human macrophages were obtained from CD14-positive cells isolated by negative selection (Pan Monocyte Isolation Kit, Miltenyi Biotec), from buffy coats of healthy donors (obtained according to a protocol approved by the S.R.S.I. Ethical Committee) and differentiated in IMDM, supplemented with 5% human serum, 4 mM glutamine, penicillin and streptomycin 100 IU/mL for 7 days. The purity of CD14-positive cells was determined by flow cytometry and was >90%. CD14-positive monocytes were differentiated in Dendritic cells by 7 day culture in the presence hGM-CFS 100 ng/mL and hIL4 10 ng/ml. All cells were maintained in a 5% $CO_2$ humidified atmosphere at 37° C. All cell lines were routinely tested for mycoplasma contamination. Human primary macrophages and 293T were transduced for 1 hour with spinoculation (at 1,100 g, at 37° C.), then washed with PBS and cultured for 3 days.

Gene Disruption and Mismatch-Selective Endonuclease Assay

Gene disruption was performed by calcium phosphate-mediated transient transfection of the indicated amount of the desired sgRNA-expressing plasmid and the Cas9-expressing plasmid. The mismatch-selective endonuclease assay was used to measure the extent of mutations consequent to non-homologous end joining (NHEJ) at the Cas9 target sites (Lombardo, A. et al. (2011) Nat Methods 8:861-869). PCR was performed using primers flanking the sgRNA binding site in the CD47 gene (fw: 5'-TTCCTTTCCAGGATCAGCTCAGC-3' (SEQ ID NO: 15); rv: 5'-TTGATTCAAAGGAGTACCTATCCC-3' (SEQ ID NO: 16)). The PCR product was denatured, allowed to re-anneal and digested with Surveyor nuclease assay (Transgenomic). Because this enzyme cuts DNA at sites of duplex distortions, the products of re-annealing between wild type and mutant alleles (carrying mutations or deletions consequent to the nuclease activity) are specifically digested. The reaction products were separated on a Spreadex EL1200 Wide Mini gel (Elchrom Scientific), stained by ethidium bromide or GelRed (Biotium) and the intensity of the bands was quantified by ImageQuant TL 5 software. The ratio of the uncleaved parental fragment to the two lower migrating cleaved products was calculated using the formula (1-(parental fraction) 1/2)×100.

Flow Cytometry

Flow cytometry analyses were performed using a FACSCanto analyser (BD Biosciences), equipped with DIVA Software. Between 100,000-500,000 cells were harvested, washed with PBS or MACS buffer (PBS pH 7.2 0.5% BSA, 2 mM EDTA), treated with Fc Receptor-Block (Miltenyi Biotec) when antibody stained and then re-suspended in the buffer used for washing. Staining was performed in MACS buffer, incubating cells with antibodies (in the proportion indicated in the table below) for 20 minutes at 4° C. in the dark. Anti-murine IgG beads were used for single-staining controls (BD Biosciences). Anti-CD47 Pacific Blue (BD Biosciences, B6H12, 1:20).

Electron Microscopy

A few microliters of concentrated LV batches were adsorbed on glow discharged carbon coated formvar copper grids and fixed for 20 minutes with 8% paraformaldehyde in PBS. After several washes in 50 mM glycine in PBS, grids were blocked in 1% BSA in PBS and incubated with primary antibodies diluted in blocking buffer for 30-90 minutes (Anti-VSV.G, KeraFAST, 1:50, Anti-CD47, BD Biosciences, 1:10). After several washes in 0.1% BSA in PBS, samples were incubated for 30 minutes with Protein A-gold (10 nm), fixed with 1% glutaraldehyde, stained with 2% uranyl acetate and air-dried. Grids were observed with a Zeiss LEO 512 transmission electron microscope. Images were acquired by a 2 k×2 k bottom-mounted slow-scan Proscan camera controlled by EsivisionPro 3.2 software. For quantification of labelling density, random images of viral particles were taken at nominal magnification of 16 k and gold particles associated to virions were manually counted using ImageJ. Virions were defined based on expected size (approximately 120 nm) and an electron-dense core.

Cytokine ELISA

The concentrations of cytokines and chemokines were determined in mouse serum by a magnetic-based multiplex ELISA 23 analytes (Bio-Plex 23-Plex, Group I, Biorad) following the manufacturer's instructions.

VCN Determination

For human macrophage experiments, DNA was extracted using QIAamp DNA Micro Kit (Qiagen), following the manufacturer's instructions. For mice experiments, DNA was extracted from whole liver or whole spleen samples using Maxwell 16 Tissue DNA Purification Kit (Promega), DNA was extracted from fractionated/sorted liver cells using DNeasy Blood & Tissue Kit (Qiagen) or QIAamp DNA Micro Kit (Qiagen), according to cell number. VCN was determined in human macrophages as described above (see "LV titration"). Human primary macrophages were transduced with LV produced by stable LV-producer cell lines, thus lacking plasmid contamination. VCN in murine DNA was determined by ddPCR, starting from 5-20 ng of template gDNA using a primers/probe set designed on the primer binding site region of LV (see "LV titration" above). The amount of endogenous murine DNA was quantified by a primers/probe set designed on the murine sema3a gene (Sema3A fw: 5'-ACCGATTCCAGATGATTGGC-3' (SEQ ID NO: 17); Sema3A 5'-rv: TCCATAT-TAATGCAGTGCTTGC-3' (SEQ ID NO: 18); Sema3A probe: HEX 5'-AGAGGCCTGTCCTGCAGCTCATGG-3' (SEQ ID NO: 19) BHQ1). The PCR reaction was performed with each primer (900 nM) and the probe (250 nM) following the manufacturer's instructions (Biorad), read with QX200 reader and analysed with QuantaSoft software (Biorad).

ImageStream

LV entry in primary human macrophages and in 293T cells was analysed by imaging flow cytometry using ImagestreamX MarkII System (Amnis, Merck). The instrument is equipped with 3 lasers (405 nm, 488 nm and 642 nm), 6-channel CCD camera, Multimag option but no extended depth of field option. Excitation laser settings were the following: 405 nm (10 mW), 488 nm (200 mW). At least 5000 events were collected for each sample with the 60X_0.9NA objective, low speed, and the images were analysed using IDEAS 6.2 software. Single-stained samples were acquired with the identical laser settings of the samples but without bright-field illumination and side scatter illumination, and were used for compensation.

Intravital Imaging

C57BL/6 or NOD mice were surgically prepared for liver IV2PM as described (Benechet, A. P. et al. (2017) Methods Mol Biol 1514:49-61). Mice were intravenously injected with PE-conjugated anti-F4/80 antibody (clone BM8, Biolegend) 20 min before imaging. GFP-labelled LV, CD47hi or CD47-free LV were intravenously injected 2 min after the start of video recording. Images (TriMScope II) were obtained with a Nikon Ti-U fluorescence inverted microscope and a 25× objective (NA 0.95). For four-dimensional analysis, 8-12 z-stacks (spacing 4 μm) of 300- to 400-μm2 xy-sections were acquired every 20 seconds for 40 min. Liver sinusoids were visualised by intravenously injecting non-targeted Quantum Dots 655 (Invitrogen) immediately prior to imaging. Sequences of image stacks were transformed into volume-rendered four-dimensional videos using Imaris software (Bitplane).

Statistical Analysis

Statistical analyses were performed upon consulting with professional statisticians at the San Raffaele University Center for Statistics in the Biomedical Sciences (CUSSB). When normality assumptions were not met, non-parametric statistical tests were performed. Mann-Whitney or Kruskall-Wallis tests were performed when comparing 2 or more experimental groups, respectively. For repeated measures over time, two-way ANOVA was performed. For paired observations, the Wilcoxon matched pairs test was performed.

All publications mentioned in the above specification are herein incorporated by reference. Various modifications and variations of the disclosed viral particles, cells, compositions, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. An enveloped viral particle producer or packaging cell, wherein:
   (a) the producer or packaging cell is genetically engineered to suppress expression of cluster of differentiation 47 (CD47); or
   (b) the producer or packaging cell comprises a genetically engineered disruption of a gene encoding CD47, to decrease expression of CD47 on the surface of the cell, and wherein the producer or packaging cell comprises one or more nucleic acid sequences encoding one or more viral particle structural proteins.

2. The enveloped viral particle producer or packaging cell of claim 1, wherein the cell is further genetically engineered to decrease expression of major histocompatibility complex I (MHC-I) on the surface of the cell.

3. The enveloped viral particle producer or packaging cell of claim 1, wherein the cell comprises a genetically engineered disruption of a gene encoding β2-microglobulin and/or a genetically engineered disruption of one or more genes encoding an MHC-I α chain.

4. The enveloped viral particle producer or packaging cell of claim 1, wherein the cell is a human embryonic kidney 293 (HEK-293) cell or a derivative thereof.

5. The enveloped viral particle producer or packaging cell of claim 1, wherein the enveloped viral particle is a retroviral, herpes simplex viral, vaccinia viral, hepadnaviral, togaviral, flaviviral, arenaviral, coronaviral, orthomyxoviral, paramyxoviral, bunyaviral, bornaviral, rhabdoviral or filoviral particle, or a viral particle derived therefrom.

6. The enveloped viral particle producer or packaging cell of claim 1, wherein the enveloped viral particle is a retroviral, herpes simplex viral or vaccinia viral particle, or a viral particle derived therefrom.

7. A method of producing enveloped viral particles comprising the steps of:

(a) providing an enveloped viral particle producer cell according to claim 1; and (b) culturing the cell under conditions suitable for the production of the enveloped viral particles.

8. An enveloped viral particle obtainable by the method of claim 7.

9. The enveloped viral particle of claim 8, wherein the viral particle is a retroviral, herpes simplex viral or vaccinia viral particle, or a viral particle derived therefrom.

10. An isolated cell transduced by the enveloped viral particle of claim 8.

11. A pharmaceutical composition comprising the enveloped viral particle of claim 8 or comprising an isolated cell transduced by said enveloped viral particle, and a pharmaceutically-acceptable carrier, diluent or excipient.

12. A method of treatment of cancer, bacterial or viral infection, an immune-mediated disease or autoimmune disease comprising transducing an isolated cell with the enveloped viral particle of claim 8.

13. A method of treatment of cancer, bacterial or viral infection, an immune-mediated disease or autoimmune disease comprising administering the enveloped viral particle of claim 8, or administering an isolated cell transduced by the enveloped viral particle, to a subject in need thereof.

14. A method of vaccination comprising administering the enveloped viral particle of claim 8 to a subject in need thereof.

15. The enveloped viral particle producer or packaging cell of claim 1, wherein the cell is a HEK-293T or a HEK-293 T-REx cell.

16. The enveloped viral particle producer or packaging cell of claim 1, wherein the enveloped viral particle is a lentiviral particle or a viral particle derived therefrom.

17. The enveloped viral particle of claim 8, wherein the enveloped viral particle is a lentiviral particle or a viral particle derived therefrom.

18. The enveloped viral particle producer or packaging cell of claim 1, wherein the number of surface-exposed CD47 molecules is less than about 10% of the number of surface-exposed CD47 molecules that are displayed in the absence of the genetic engineering.

\* \* \* \* \*

SEQUENCE LISTING

```
<160> NUMBER OF SEQ ID NOS: 19

<210> SEQ ID NO 1
<211> LENGTH: 323
<212> TYPE: PRT
<213> ORGANISM: Homo sapiens

<400> SEQUENCE: 1

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220
```

```
Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 2
<211> LENGTH: 292
<212> TYPE: PRT
<213> ORGANISM: Homo sapiens

<400> SEQUENCE: 2

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270
```

Ser Gly Leu Ser Ile Leu Ala Leu Ala Gln Leu Leu Gly Leu Val Tyr
        275                 280                 285

Met Lys Phe Val
    290

<210> SEQ ID NO 3
<211> LENGTH: 305
<212> TYPE: PRT
<213> ORGANISM: Homo sapiens

<400> SEQUENCE: 3

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305

<210> SEQ ID NO 4
<211> LENGTH: 311
<212> TYPE: PRT
<213> ORGANISM: Homo sapiens

<400> SEQUENCE: 4

| | | | | | | | | | | | | | | |
|---|---|---|---|---|---|---|---|---|---|---|---|---|---|---|
|Met|Trp|Pro|Leu|Val|Ala|Ala|Leu|Leu|Leu|Gly|Ser|Ala|Cys|Cys|Gly|
|1| | | |5| | | | |10| | | | |15| |

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
            85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
            165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
            245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn
305                 310

<210> SEQ ID NO 5
<211> LENGTH: 972
<212> TYPE: DNA
<213> ORGANISM: Artificial Sequence
<220> FEATURE:
<223> OTHER INFORMATION: nucleotide sequence encoding human CD47

<400> SEQUENCE: 5

```
atgtggcccc tggtagcggc gctgttgctg ggctcggcgt gctgcggatc agctcagcta      60
ctatttaata aaacaaaatc tgtagaattc acgttttgta atgacactgt cgtcattcca     120
tgctttgtta ctaatatgga ggcacaaaac actactgaag tatacgtaaa gtggaaattt     180
```

```
aaaggaagag atatttacac ctttgatgga gctctaaaca agtccactgt ccccactgac    240
tttagtagtg caaaaattga agtctcacaa ttactaaaag gagatgcctc tttgaagatg    300
gataagagtg atgctgtctc acacacagga aactacactt gtgaagtaac agaattaacc    360
agagaaggtg aaacgatcat cgagctaaaa tatcgtgttg tttcatggtt ttctccaaat    420
gaaaatattc ttattgttat tttcccaatt tttgctatac tcctgttctg gggacagttt    480
ggtattaaaa cacttaaata tagatccggt ggtatggatg agaaaacaat tgctttactt    540
gttgctggac tagtgatcac tgtcattgtc attgttggag ccattctttt cgtcccaggt    600
gaatattcat taagaatgc tactggcctt ggtttaattg tgacttctac agggatatta    660
atattacttc actactatgt gtttagtaca gcgattggat taacctcctt cgtcattgcc    720
atattggtta ttcaggtgat agcctatatc ctcgctgtgg ttggactgag tctctgtatt    780
gcggcgtgta taccaatgca tggccctctt ctgatttcag gtttgagtat cttagctcta    840
gcacaattac ttggactagt ttatatgaaa tttgtggctt ccaatcagaa gactatacaa    900
cctcctagga aagctgtaga ggaaccccctt aatgcattca agaatcaaa aggaatgatg    960 aatgatgaat aa                                                        972
```

<210> SEQ ID NO 6
<211> LENGTH: 23
<212> TYPE: DNA
<213> ORGANISM: Artificial Sequence
<220> FEATURE:
<223> OTHER INFORMATION: sequence used to generate the sgRNA, CD47 A

<400> SEQUENCE: 6

```
ctactgaagt atacgtaaag tgg                                             23
```

<210> SEQ ID NO 7
<211> LENGTH: 23
<212> TYPE: DNA
<213> ORGANISM: Artificial Sequence
<220> FEATURE:
<223> OTHER INFORMATION: sequence used to generate the sgRNA, CD47 B

<400> SEQUENCE: 7

```
cttgtttaga gctccatcaa agg                                             23
```

<210> SEQ ID NO 8
<211> LENGTH: 23
<212> TYPE: DNA
<213> ORGANISM: Artificial Sequence
<220> FEATURE:
<223> OTHER INFORMATION: sequence used to generate the sgRNA, CD47 C

<400> SEQUENCE: 8

```
atcgagctaa aatatcgtgt tgg                                             23
```

<210> SEQ ID NO 9
<211> LENGTH: 18
<212> TYPE: DNA
<213> ORGANISM: Artificial Sequence
<220> FEATURE:
<223> OTHER INFORMATION: primer HIV fw

<400> SEQUENCE: 9

```
tactgacgct ctcgcacc                                                   18
```

<210> SEQ ID NO 10
<211> LENGTH: 17

```
<212> TYPE: DNA
<213> ORGANISM: Artificial Sequence
<220> FEATURE:
<223> OTHER INFORMATION: primer HIV rv

<400> SEQUENCE: 10
tctcgacgca ggactcg                                                17

<210> SEQ ID NO 11
<211> LENGTH: 20
<212> TYPE: DNA
<213> ORGANISM: Artificial Sequence
<220> FEATURE:
<223> OTHER INFORMATION: probe designed on primer binding site region of
      LV

<400> SEQUENCE: 11
atctctctcc ttctagcctc                                             20

<210> SEQ ID NO 12
<211> LENGTH: 18
<212> TYPE: DNA
<213> ORGANISM: Artificial Sequence
<220> FEATURE:
<223> OTHER INFORMATION: primer Telo fw

<400> SEQUENCE: 12
ggcacacgtg gcttttcg                                               18

<210> SEQ ID NO 13
<211> LENGTH: 24
<212> TYPE: DNA
<213> ORGANISM: Artificial Sequence
<220> FEATURE:
<223> OTHER INFORMATION: primer Telo rv

<400> SEQUENCE: 13
ggtgaacctc gtaagtttat gcaa                                        24

<210> SEQ ID NO 14
<211> LENGTH: 24
<212> TYPE: DNA
<213> ORGANISM: Artificial Sequence
<220> FEATURE:
<223> OTHER INFORMATION: Telo probe

<400> SEQUENCE: 14
tcaggacgtc gagtggacac ggtg                                        24

<210> SEQ ID NO 15
<211> LENGTH: 23
<212> TYPE: DNA
<213> ORGANISM: Artificial Sequence
<220> FEATURE:
<223> OTHER INFORMATION: primer fw, sgRNA binding site in the CD47 gene

<400> SEQUENCE: 15
ttcctttcca ggatcagctc agc                                         23

<210> SEQ ID NO 16
<211> LENGTH: 24
<212> TYPE: DNA
<213> ORGANISM: Artificial Sequence
<220> FEATURE:
<223> OTHER INFORMATION: primer rv, sgRNA binding site in the CD47 gene

<400> SEQUENCE: 16
```

```
ttgattcaaa ggagtaccta tccc                                          24

<210> SEQ ID NO 17
<211> LENGTH: 20
<212> TYPE: DNA
<213> ORGANISM: Artificial Sequence
<220> FEATURE:
<223> OTHER INFORMATION: primer fw, Sema3A gene

<400> SEQUENCE: 17
accgattcca gatgattggc                                               20

<210> SEQ ID NO 18
<211> LENGTH: 22
<212> TYPE: DNA
<213> ORGANISM: Artificial Sequence
<220> FEATURE:
<223> OTHER INFORMATION: primer rv, Sema3A gene

<400> SEQUENCE: 18
tccatattaa tgcagtgctt gc                                            22

<210> SEQ ID NO 19
<211> LENGTH: 24
<212> TYPE: DNA
<213> ORGANISM: Artificial Sequence
<220> FEATURE:
<223> OTHER INFORMATION: Sema3A gene probe

<400> SEQUENCE: 19
agaggcctgt cctgcagctc atgg                                          24
```